(12) United States Patent
Kawano et al.

(10) Patent No.: US 7,798,958 B2
(45) Date of Patent: Sep. 21, 2010

(54) MEDICAL DEVICE CONTROL SYSTEM

(75) Inventors: Hironao Kawano, Tokyo (JP); Akio Uchiyama, Kanagawa (JP); Hironobu Takizawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 878 days.

(21) Appl. No.: 11/630,730

(22) PCT Filed: Sep. 6, 2006

(86) PCT No.: PCT/JP2006/317669
§ 371 (c)(1),
(2), (4) Date: Dec. 21, 2006

(87) PCT Pub. No.: WO2008/029460
PCT Pub. Date: Mar. 13, 2008

(65) Prior Publication Data
US 2008/0319262 A1 Dec. 25, 2008

(51) Int. Cl.
*A61B 1/00* (2006.01)
(52) U.S. Cl. .................... 600/118; 600/117; 600/101; 600/424
(58) Field of Classification Search .............. 600/101, 600/117, 118, 407, 424
See application file for complete search history.

(56) References Cited
U.S. PATENT DOCUMENTS

| | | | |
|---|---|---|---|
| 2003/0229268 A1* | 12/2003 | Uchiyama et al. | 600/109 |
| 2004/0138552 A1* | 7/2004 | Harel et al. | 600/407 |
| 2004/0181127 A1* | 9/2004 | Matsumoto et al. | 600/101 |
| 2004/0236180 A1* | 11/2004 | Uchiyama et al. | 600/109 |
| 2005/0062562 A1* | 3/2005 | Ries | 335/1 |
| 2005/0085696 A1* | 4/2005 | Uchiyama et al. | 600/160 |
| 2005/0093544 A1* | 5/2005 | Ries | 324/318 |
| 2005/0216231 A1* | 9/2005 | Aoki et al. | 702/183 |
| 2006/0152309 A1* | 7/2006 | Mintchev et al. | 335/58 |
| 2006/0270903 A1* | 11/2006 | Uchiyama et al. | 600/118 |

FOREIGN PATENT DOCUMENTS

| | | |
|---|---|---|
| JP | 2003-111720 | 4/2003 |
| JP | 2004-255174 | 9/2004 |
| JP | 2005-245963 | 9/2005 |
| WO | WO 00/07641 | 2/2000 |

* cited by examiner

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

A medical device control system improves an inducing stability and operability of a medical device having its direction controlled with magnetism, which is used for the inspection or treatment in a subject's body. The control system is formed of a medical device including an insertion member inserted into the subject's body, and a magnetic field response portion disposed within the insertion member for generating torque in response to the magnetic field applied from outside the subject's body, a direction detection unit that detects an insertion direction of the insertion member, a user interface through which the information with respect to the control of the insertion direction is input and output, a magnetic field generation portion that generates a magnetic field that directs the insertion member to a control direction, and a user interface control unit that controls the user interface based on a discordance between the control direction and the insertion direction.

27 Claims, 26 Drawing Sheets

MEDICAL DEVICE CONTROL SYSTEM

BACKGROUND OF THE INVENTION

1. Field of the Invention

The invention relates to a medical device control system.

2. Description of Related Art

Recently, there has been research and development of swallowable capsule medical devices, as represented by capsule endoscopes and the like, that are swallowed by a subject to enter the subject's body, where they traverse a passage in the body cavity to capture images of a target site inside the passage in the body cavity. The capsule endoscopes described above have a configuration in which an imaging device that can perform the medical procedure described above, for example, a CCD (Charge Coupled Device) that can acquire images or the like, is provided and perform image acquisition at the target site inside the passage in the body cavity.

The aforementioned capsule medical device may only be moved through the digestive tract by action of peristalsis but not controlled with respect to its position and direction. Location of the capsule medical device within the passage in the body cavity has been required to induce the capsule medical device so as to be allowed to perform easy diagnosis.

The technique for locating the medical device that has been induced to the site (within the passage in the body cavity) that cannot be visually identified so as to be further induced to the target site has been disclosed in Japanese Unexamined Patent Application, publication No. 2004-25174 (hereinafter referred to as Patent Document 1).

The above-described technique is required not only for the capsule medical device but also for the medical device equipped with the probe that is induced into the passage in the cavity of the subject's body. The technique for locating the medical device that has been induced to the site (within the passage in the body cavity) that cannot be visually identified so as to be further guided to the target site has also been disclosed in PCT International Publication No. WO00/07641 (Pamphlet) (hereinafter referred to as Patent Document 2).

BRIEF SUMMARY OF THE INVENTION

The disclosure of Patent Document 1 relates to the system for controlling the medical device inserted into the body cavity with the magnetic field. According to the disclosure, the magnetic field to be generated for controlling the medical device is determined based on the direction information obtained by the device for detecting the direction of the medical device.

Patent Document 1 discloses only the concept with respect to determination of the magnetic field generated for the medical device based on the direction information detected by the device for detecting the direction of the medical device without proposing the specific process for such determination. Likewise Patent Document 2, it tends to deteriorate controllability (inducing stability, operability) of the medical device when a large discordance occurs between direction of the medical device and the magnetic field direction.

Patent Document 2 discloses the technique that allows the operator to command and determine the direction for generating the magnetic field while confirming the position and direction of the catheter using the fluoroscope.

Since the information on the position and direction of the catheter is acquired as the image information such that the operator reads the displayed image information to command and determine the direction for generating the magnetic field, the position and direction information cannot be constantly monitored.

This may fail to prevent the large discordance in the direction between the catheter and the magnetic field. In the case where the large discordance in the direction occurs between the catheter and magnetic field, the controllability (inducing stability and operability) of the catheter may be deteriorated.

Japanese Unexamined Patent Application, Publication No. 2003-111720 relates to the control such that the force acting on the intra-body robot becomes proportional to the force acting on the input device. The resultant system becomes complicated because of the requirement for calculating the force acting on the intra-body robot.

It is an object of the present invention to provide a medical device control system that improves inducing stability and operability with respect to the medical device used for performing the inspection or treatment of the subject's body under the direction control with the magnetic field.

The present invention provide following means for the purpose of achieving the aforementioned object.

A first aspect of the present invention provides a medical device control system formed of a medical device including an insertion member inserted into a subject's body and a magnetic field response portion that generates torque in response to a magnetic field applied from outside the subject's body, a direction detection unit that detects an insertion direction of the insertion member, a user interface through which information with respect to a control of the insertion direction is input and output, a magnetic field generation portion that acts on the magnetic field response portion to generate the magnetic field that directs the insertion member to a control direction, and a user interface control unit that controls the user interface based on a discordance between the control direction and the insertion direction.

According to the first aspect of the invention, the user interface control unit controls the user interface based on the discordance. The discordance, thus, may be transferred to the outside via the user interface. For example, it is possible to feedback the discordance to the operator who inputs the control direction to the user interface, thus improving the inducing stability and operability of the medical device.

In the first aspect of the present invention, preferably, the user interface is provided with an operation unit through which an operator commands the insertion direction, and the operation unit is provided with a discordance information transmission portion controlled by the user interface control unit for transmitting the discordance to the operator.

The discordance may be transferred to the operator from the discordance information transfer unit provided in the operation unit. The discordance may be easily feedbacked to the operator, improving the operability of the insertion member.

Preferably, the discordance information transfer unit is formed as an oscillating body.

The information based on the discordance may be transferred to the outside as the oscillation generated by the oscillating unit. For example, the frequency of the generated oscillation may be increased as the discordance becomes large. Meanwhile, the frequency of the oscillation may be decreased as the discordance becomes small so as to transfer the information based on the discordance.

In the aforementioned structure, preferably, the operation unit is provided with a movable body through which the control direction is input, and the discordance information transmission portion is a reaction force generation portion that generates a force in a direction opposite a movement of the movable body.

When the control direction is input by moving the movable body, the reaction force generating unit generates the force (reaction force) acting in the direction opposite the moving direction of the movable body so as to notify the operator of the discordance. For example, when the discordance becomes large, the reaction force with respect to the movement of the movable body is increased. Meanwhile, when the discordance becomes small, the reaction force is decreased. This makes it possible to notify the operator of the level of the discordance. The operability of the movable body may be improved since the operator is allowed to perform the realistic operation.

In the aforementioned structure, preferably, the operation unit is provided with a movable body through which the control direction is input, and the discordance information transmission portion is a load generating portion that generates a load to a movement of the movable body.

When the control direction is input by moving the movable body, the load generation unit generates the load to the movement of the movable body so as to notify the operator of the discordance. For example, when the discordance becomes large, the load to the movement of the movable body is increased. Meanwhile, when the discordance becomes small, the load is decreased. This makes it possible to notify the operator of the level of the discordance. The operability of the movable body may be improved since the operator is allowed to perform the realistic operation.

The operation unit may be formed more easily compared to the process for generating the force in the direction opposite the movement of the movable body.

According to the first aspect of the present invention, preferably, the user interface is provided with a display unit that displays the insertion direction and the discordance, and the display unit is controlled by the user interface control unit.

The display unit provided for the user interface may be controlled by the user interface control unit. As the insertion direction and the discordance are displayed on the display unit, the operator may be notified of the discordance. The discordance may be easily feedbacked to the operator who inputs the control direction, thus improving the operability of the insertion member.

According to the first aspect of the invention, the user interface is provided with a display unit that displays the insertion direction and the discordance, and the display unit is controlled by the user interface control unit. Further, the display unit displays information of the insertion direction and information of the control direction superimposed thereon.

The superimposed image of the insertion direction and the control direction may be displayed on the display unit. This allows the operator who inputs the control direction to identify the control state intuitively, thus improving the operability of the insertion member.

According to the first aspect of the present invention, the user interface is provided with a display unit that displays the insertion direction and the discordance, and the display unit is controlled by the user interface control unit. Preferably, the display unit displays the discordance between the insertion direction and the control direction.

The discordance of the control direction from the inserting direction is displayed such that the operator who inputs the control direction may be easily notified of the control state.

For example, the discordance amount may be displayed as the numerical data, length, vector and the like. Alternatively, the alarm signal may be displayed when the discordance exceeds the predetermined discordance value, or when a predetermined time period elapses in the state where the discordance is kept in excess of the predetermined discordance.

According to the first aspect of the invention, preferably, a magnetic field control unit that controls the magnetic field generation portion is provided, and the magnetic field control unit controls the magnetic field generation portion such that a value of the discordance is equal to or smaller than a predetermined value. More preferably, a magnetic field control unit that controls the magnetic field generation portion is provided, and the magnetic field control portion controls the magnetic field generation portion such that a value of the discordance is equal to or smaller than a predetermined value, and further the magnetic field control unit includes a predetermined value change portion that changes the predetermined value with a finite value.

The magnetic field generation portion is controlled by the magnetic field control unit for controlling the magnetic field direction such that the discordance does not exceed the predetermined value. This may prevent deterioration in the operability of the insertion member due to excessive increase in the discordance.

The predetermined value change portion changes the predetermined value to a finite value. This makes it possible to prevent the discordance from exceeding the range that can be controlled by the medical unit control system. Further, the predetermined value may be defined in accordance with the medical unit control system so as to reliably prevent deterioration in the operability of the insertion member.

A second aspect of the invention provides a medical device control system formed of a medical device including an insertion member inserted into a subject's body, having its direction controlled by magnetism, and a magnetic field response portion disposed within the insertion member for generating torque in response to a magnetic field applied from outside the subject's body, a direction detection unit that detects an insertion direction of the insertion member, a user interface through which a control direction for the insertion direction is input by an operator, a magnetic field generation portion that generates a magnetic field that acts on the magnetic field response portion, and a magnetic field control unit that controls the magnetic field generation portion based on a discordance between the insertion direction and the control direction.

In the second aspect of the invention, the magnetic field may be controlled by the magnetic field control unit based on the discordance, thus preventing deterioration in the operability of the insertion member. In the case where the magnetic field generated by the magnetic field generation portion is not suitable for inducing the insertion member toward the control direction, and the discordance becomes large, the magnetic field may be changed to the one suitable for inducing the insertion member. This makes it possible to prevent increase in the discordance.

According to the second aspect of the invention, preferably, the magnetic field control unit includes a magnetic field pattern storage portion that stores a plurality of magnetic field generation patterns, and a magnetic field pattern change portion that selects a magnetic field pattern from the plurality of magnetic field generation patterns so as to be generated based on the discordance, and changes the magnetic field pattern generated by the magnetic field generation portion to the selected magnetic field pattern.

Among the plurality of magnetic field patterns stored in the magnetic field pattern storage unit, the one suitable for controlling the operation unit is selected by the magnetic field pattern change unit based on the discordance such that the magnetic field pattern is changed to the selected one that has been generated by the magnetic field generation portion. In the case where the magnetic field pattern is not suitable for inducing the insertion member toward the control direction, and the discordance becomes large, the magnetic field pattern suitable for inducing the insertion member is selected to be changed. This makes it possible to prevent increase in the discordance such that the deterioration in the operability of the insertion member may be further prevented.

In the aforementioned structure, preferably, the magnetic field response portion is a magnet or an electromagnet that exhibits a magnetization direction substantially perpendicular to the insertion direction, and one of the plurality of magnetic field patterns stored in the magnetic field pattern storage portion is a revolving magnetic field that revolves on a plane substantially perpendicular to the control direction.

The magnetic field response portion is formed as a magnet that exhibits magnetization direction substantially perpendicular to the insertion direction. The revolving magnetic field is activated to rotate the magnet such that the insertion member is rotated around the rotating axis along the direction for inserting the insertion member.

The insertion member is rotatably driven to control the insertion member reliably compared to the magnetic field generated by combining the revolving magnetic field and the oscillating magnetic field, or the revolving magnetic field.

In the aforementioned structure, preferably, the magnetic field response portion is a magnet or an electromagnet that exhibits a magnetization direction substantially perpendicular to the insertion direction, and one of the plurality of magnetic field patterns stored in the magnetic field pattern storage portion is a magnetic field formed by combining a revolving magnetic field that revolves on a plane substantially perpendicular to the control direction and an oscillating magnetic field that oscillates substantially in parallel to the control direction.

The magnetic response portion is formed as the magnet that exhibits the magnetization direction substantially perpendicular to the insertion member. The magnetic field pattern formed by combining the revolving magnetic field and the oscillating magnetic field is activated on the magnetic field response portion to control the revolving plane in the revolving magnetic field toward the predetermined direction. This makes it possible to swing the insertion member around the axis along the inserting direction while revolving its leading end.

In the case where the insertion member is inserted into the narrowed passage of the body cavity, the insertion member is swingably revolved while widening the passage of the body cavity. This makes it possible to allow penetration of the insertion member into the widened passage of the body cavity.

In the aforementioned structure, preferably, the magnetic field response portion is a magnet or an electromagnet that exhibits a magnetization direction substantially perpendicular to the insertion direction. One of the plurality of magnetic field patterns stored in the magnetic field pattern storage portion is a fluctuating magnetic field having its direction fluctuated on a plane substantially perpendicular to the control direction. An angle formed by an intersection line of a plane substantially perpendicular to the control direction with a plane that contains the insertion direction and the control direction, and the magnetic field direction of the fluctuating magnetic field varies within a predetermined range.

The magnetic field response portion is formed as the magnet that exhibits the magnetization direction substantially perpendicular to the insertion member. As the fluctuation magnetic field having the magnetic field direction fluctuating within the predetermined range is activated on the magnetic field response portion, the torque constantly acts to direct the insertion member toward the predetermined range.

For example, the predetermined range may be made accorded with the control direction of the insertion member so as to constantly generate the torque for directing the insertion member toward the control direction, thus efficiently changing the direction of the insertion member.

In the aforementioned structure, the magnetic field response portion is a magnet or an electromagnet that exhibits a magnetization direction substantially perpendicular to the insertion direction. One of the plurality of magnetic field patterns stored in the magnetic field pattern storage portion is a fluctuating magnetic field having its direction fluctuated on a plane substantially perpendicular to the control direction. An angle formed by an intersection line of a plane substantially perpendicular to the control direction with a plane that contains the insertion direction and the control direction, and the magnetic field direction of the fluctuating magnetic field varies within a predetermined range. Preferably, an intensity of the fluctuating magnetic field is kept constant, and an angle formed by the direction of the fluctuating magnetic field, and the intersection line varies continuously within a predetermined range.

In the aforementioned structure, as the angle defined by the magnetic field direction of the fluctuation magnetic field and the intersection continuously changes within the predetermined range, the position of the insertion member may be reliably controlled compared to the case where such angle changes intermittently.

In the aforementioned structure, preferably, the magnetic field pattern change portion generates a magnetic field pattern having the magnetic field revolved on a plane substantially perpendicular to the insertion direction subsequent to the magnetic field pattern currently generated by the magnetic field generation portion, and further generates a next magnetic field pattern thereafter.

The magnetic field pattern that has been currently generated may be changed to the different one by generating the magnetic field pattern having the magnetic field revolved on the plane substantially perpendicular to the insertion direction. Thereafter, the different magnetic field pattern is generated so as to keep the reliable control for the insertion member.

The magnetic field pattern is changed via the magnetic field pattern that revolves and is controllable with respect to the inserting direction reliably.

In the aforementioned structure, preferably, the magnetic field response portion is a magnet or an electromagnet that exhibits a magnetization direction substantially perpendicular to the insertion direction. One of the plurality of magnetic field patterns stored in the magnetic field pattern storage portion is a fluctuating magnetic field having its direction fluctuated on a plane substantially perpendicular to the control direction. Preferably, the insertion member is substantially cylindrical, and provided with the magnetic field response portion rotatably around a center axis of the insertion member.

The magnetic field response portion is rotatably disposed with respect to the insertion member. For example, even if the magnetic field response portion is driven to rotate, the insertion member is not driven to rotate. In the case where the direction of the magnetic field response portion is changed, the direction of the insertion member may be changed accordingly.

In the aforementioned structure, preferably, the magnetic field response portion is a magnet or an electromagnet that exhibits a magnetization direction substantially perpendicular to the insertion direction. One of the plurality of magnetic field patterns stored in the magnetic field pattern storage portion is a revolving magnetic field that revolves on a plane substantially perpendicular to the control direction. Preferably, the magnetic field response portion is fixed to the insertion member.

The magnetic field response portion is fixed to the insertion member. As the magnetic field response portion is driven to rotate, the insertion member is also rotated accordingly.

In the aforementioned structure, preferably, the magnetic field response portion is a magnet or an electromagnet that exhibits a magnetization direction substantially in parallel to the insertion direction. One of the plurality of the magnetic field patterns stored in the magnetic pattern storage portion is an oscillating magnetic field that oscillates around the control direction, and an angle formed by the oscillating magnetic field and the control direction is within a predetermined range.

The magnetic field response portion is formed as a magnet directed toward magnetization substantially parallel to the insertion direction. The oscillating magnetic field where the magnetic field direction fluctuates in the predetermined range is caused to act on the aforementioned magnet such that the insertion member oscillates with respect to the control direction.

For example, the oscillating magnetic field is caused to act for swinging oscillation with respect to the control direction for the purpose of swingably oscillating the insertion member. This makes it possible to widen the nearly closed passage of the body cavity through the swingable oscillation of the insertion member, and to allow the insertion member to penetrate through the widened passage of the body cavity.

In the aforementioned structure, preferably, the magnetic field response portion is a magnet or an electromagnet that exhibits a magnetization direction substantially in parallel to the insertion direction. One of the plurality of magnetic field patterns stored in the magnetic field pattern storage portion is the magnetic field formed by combining the magnetic field substantially in parallel to the insertion direction and a revolving magnetic field that revolves on a plane substantially perpendicular to the insertion direction.

The magnetic field response portion is formed as a magnet that exhibits the magnetization direction substantially perpendicular to the insertion direction. The magnetic field pattern formed by combining the substantially parallel magnetic field and the revolving magnetic field is caused to act for the purpose of swingably rotating the insertion member with respect to the inserting direction.

In the aforementioned structure, preferably, the magnetic field response portion is a magnet or an electromagnet that exhibits a magnetization direction substantially in parallel to the insertion direction. One of the plurality of magnetic field patterns stored in the magnetic field pattern storage portion is a fluctuating magnetic field having its direction fluctuated on a plane that contains the insertion direction and the control direction.

The magnetic field response portion is formed as a magnet that exhibits the magnetization direction substantially perpendicular to the insertion direction. The magnetic pattern having the magnetic field direction changed on the aforementioned plane is caused to act for the purpose of easily directing the insertion member toward the control direction.

In the aforementioned structure, the magnetic field response portion is a magnet or an electromagnet that exhibits a magnetization direction substantially in parallel to the insertion direction. One of the plurality of the magnetic field patterns stored in the magnetic pattern storage portion is an oscillating magnetic field that oscillates around the control direction. An angle formed by the oscillating magnetic field and the control direction is within a predetermined range. Preferably, the magnetic field response portion is a magnet or an electromagnet that exhibits a magnetization direction substantially in parallel to the insertion direction. One of the plurality of magnetic field patterns stored in the magnetic field pattern storage portion is a fluctuating magnetic field having its direction fluctuated on a plane perpendicular to a plane that contains the insertion direction and the control direction.

The magnetic field response portion is formed as a magnet that exhibits the magnetization direction substantially perpendicular to the insertion direction. The magnetic field pattern having the magnetic field direction changed on the substantially perpendicular plane is caused to act for the purpose of easily directing the insertion member toward the control direction.

In the aforementioned structure, preferably, the magnetic field pattern change portion generates a magnetic field pattern having the magnetic field substantially in parallel to the insertion direction subsequent to the magnetic field pattern currently generated by the magnetic field generation portion, and further generates a next magnetic field pattern thereafter.

The magnetic field pattern currently generated is changed to the different one by generating the magnetic field pattern substantially in parallel to the direction of the insertion member. Thereafter, the different magnetic field pattern is generated to keep the stabilized operation of the insertion member.

The control stability of the insertion member may be kept by changing the magnetic field pattern via the one substantially in parallel to the direction of the insertion member, thus stabilizing the operation of the insertion member.

According to the second aspect of the present invention, preferably, the magnetic field control unit is provided with a magnetic field intensity change portion that changes an intensity of the magnetic field based on the discordance.

The force acting on the insertion member to change the direction may be increased by intensifying the magnetic field. Accordingly, in the case where the discordance becomes large, the magnetic field is increased to enable the control in the state more reliable than the case the discordance is further increased.

A third aspect of the present invention provides a medical device control system formed of a medical device including an insertion member inserted into a subject's body, and a magnetic field response portion disposed within the insertion member to generate torque in response to a magnetic field applied from outside the subject's body, a direction detection unit that detects an insertion direction of the insertion member, a magnetic field generation portion that acts on the magnetic field response portion to generate a magnetic field for directing the insertion member to a control direction, and a magnetic field control unit that controls the magnetic field generation portion such that a discordance between the insertion direction and the control direction is equal to or smaller than a predetermined value.

According to the third aspect of the invention, the magnetic field generation portion is controlled by the magnetic field control unit to regulate the magnetic field direction, thus preventing the discordance from exceeding the predetermined value. This makes it possible to avoid deterioration in the operability of the insertion member owing to the excessive discordance.

For example, even if the discordance between the direction of the insertion portion and the control direction due to the external force acting on the insertion member, the discordance may be prevented from exceeding the predetermined value by controlling the magnetic field direction.

According to the third aspect of the present invention, preferably, when the discordance exceeds the predetermined value, the magnetic field control unit controls the magnetic field generation portion such that the control direction substantially accords with the insertion direction.

When the discordance becomes large to exceed the predetermined value, the magnetic field direction is changed conforming to the direction of the insertion member at the time point. In the case where the insertion member penetrates through the passage of the internal organ, it is allowed to move forward along the wall surface of the internal organ without requiring the control information acquired through the external input.

According to the third aspect of the invention, preferably, the magnetic field control unit is provided with a predetermined value change portion that changes the predetermined value within an effective range.

The predetermined value change portion is capable of changing the predetermined value within an effective range.

According to the first to the third aspects of the invention, preferably, the insertion member includes a driving force generation portion that generates a driving force in the insertion direction.

The driving force generating unit allows the driving force to be applied to the insertion member. Especially in the case where the magnetic field control unit controls the magnetic field generation portion such that the discordance between the direction for inserting the insertion member and the control direction thereof becomes equal to or smaller than the predetermined value, when the control direction is changed by the wall of the internal organ as a result of penetration of the insertion member that has been driven, the control direction may be changed to adjust the discordance to be equal to or smaller than the predetermined value. The insertion member is automatically inserted along the wall surface of the passage in the internal organ.

In the medical device control system according to the invention, the control unit controls the user interface based on the discordance. This makes it possible to transmit the information based on the discordance to outside via the user interface. Accordingly, the information based on the discordance may be feedbacked to the operator who inputs the control direction information to the user interface, resulting in such effects as the improved inducing stability and operability of the medical device (insertion member).

Additionally, the control unit is allowed to induce the insertion member conforming to the situation for the purpose of controlling the magnetic field generation portion based on the discordance. This makes it possible to further improve the inducing performance using the simply structured system.

DETAILED DESCRIPTION OF THE INVENTION

First Embodiment

A first embodiment of the invention will be described referring to FIGS. 1 to 28.

Figure 1:
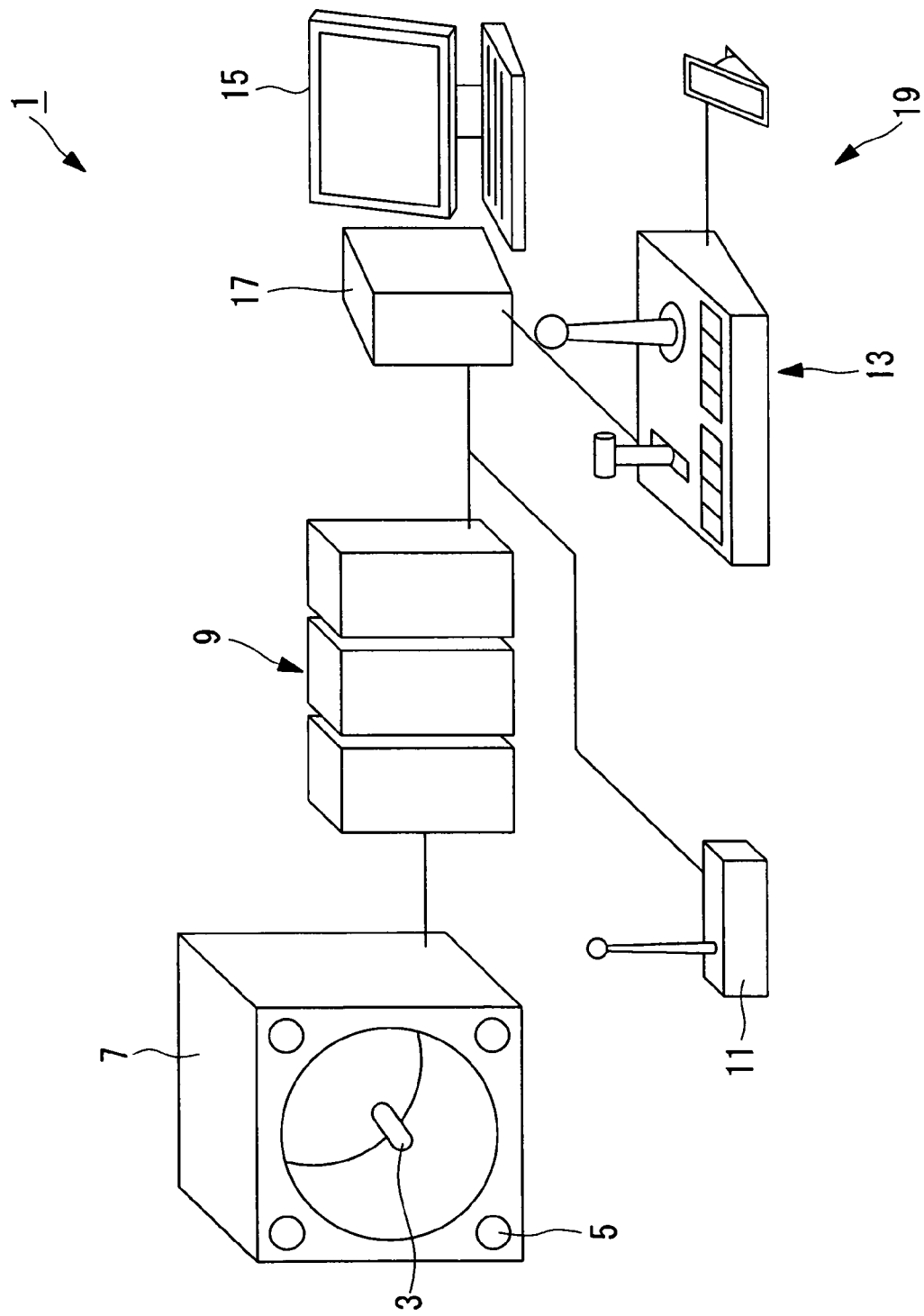
FIG. 1 is a schematic view showing a structure of a capsule endoscope control system according to the first aspect of the invention.

FIG. 1 is an explanatory view schematically showing the structure of a capsule endoscope control system of the embodiment.

A capsule endoscope control system (medical device control system) 1 includes a capsule endoscope (insertion member, medical device) 3 to be inserted into a subject's body, a position detection sensor (direction detection unit) 5 that detects information on the position or direction of the capsule endoscope 3, a triaxial Helmholtz coil (magnetic field generation portion) 7 that generates the magnetic field acting on the permanent magnet installed in the capsule endoscope 3, a power source 9 that supplies power to the triaxial Helmholts coil 7, an extracorporeal device 11 that receives the image information transmitted from the capsule endoscope 3, an operation unit 13 to which the control information to the capsule endoscope 3 is input; a display unit 15 that displays the image information transmitted from the capsule endoscope 3, and a control unit (user interface control unit) 17 that controls the triaxial Helmholts coil 7, the operation unit 13, the display unit 15, and the like.

Figure 2:
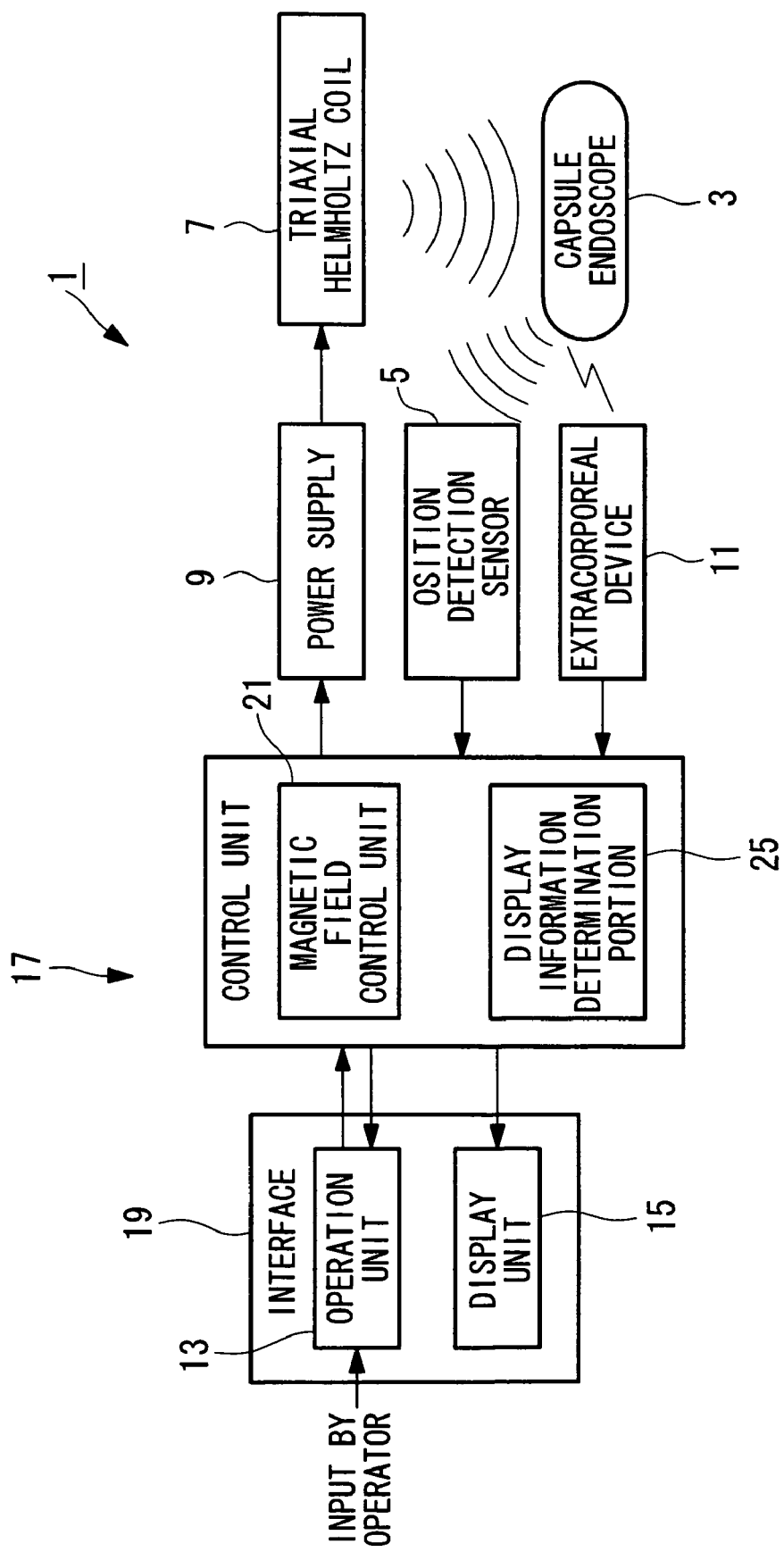
FIG. 2 is a schematic view of a system configuration of the capsule endoscope control system shown in FIG. 1.

FIG. 2 is a schematic view of the structure of the capsule endoscope control system 1 shown in FIG. 1.

The capsule endoscope control system 1 is provided with a user interface 19 which includes the operating unit 13 to which the control information input by the operator to the capsule endoscope 3 is input, and the display unit 15 that displays the image information acquired by the capsule endoscope 3. The control unit 17 includes a magnetic field control unit (magnetic field pattern storage portion, magnetic field pattern change portion, predetermined value change portion) 21 that controls the direction of the magnetic field generated by the triaxial Helmholts coil 7 based on the input control information, and a display information determination portion (user interface control unit) 25 that determines the information displayed to the user interface 19.

The power source 9 that receives control signals from the control unit 17 is disposed so as to supply power to the triaxial Helmholts coil 7 based on the control signal.

The position detection sensor 5 detects the induced magnetism generated from the capsule endoscope 3, and outputs the signal based on the detected induced magnetism to the control unit 17. The extracorporeal device 11 receives the image information obtained to be transmitted by the capsule endoscope 3 to the outside, and outputs the received image information to the control unit 17.

Figure 3:
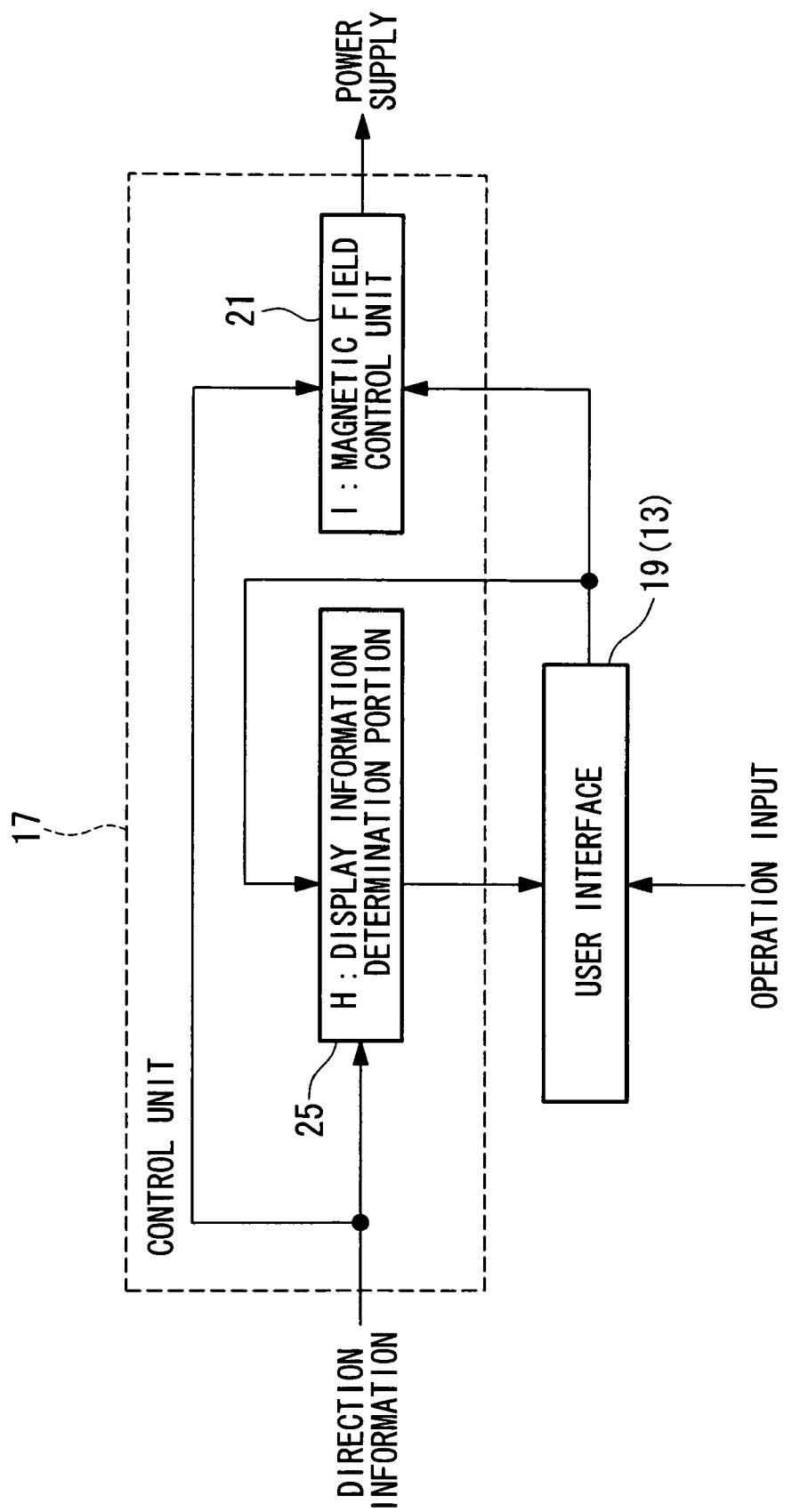
FIG. 3 is a control block diagram with respect to the capsule endoscope control system shown in FIG. 1.

FIG. 3 is a block diagram of the capsule endoscope control system 1 shown in FIG. 1.

Data with respect to the direction of the capsule endoscope 3 input from the position detection sensor 5 to the control unit 17, and the control direction of the capsule endoscope 3 (to be described later) are input to the display information determination portion 25. Then data to be output to the display unit 15 or the operation unit 13 are generated based on the discordance between the direction information and the control information.

The user interface 19 receives the input of the operator so as to determine the subsequent control direction.

The determined control direction is returned to the display information determination portion 25, and input to the magnetic field control unit 21. The direction of the capsule endoscope 3 is input to the magnetic field control unit 21 such that the power supply to be connected to the triaxial Helmholtz coil 7 is controlled based on the discordance between the control direction and the direction of the capsule endoscope 3.

Figure 4:
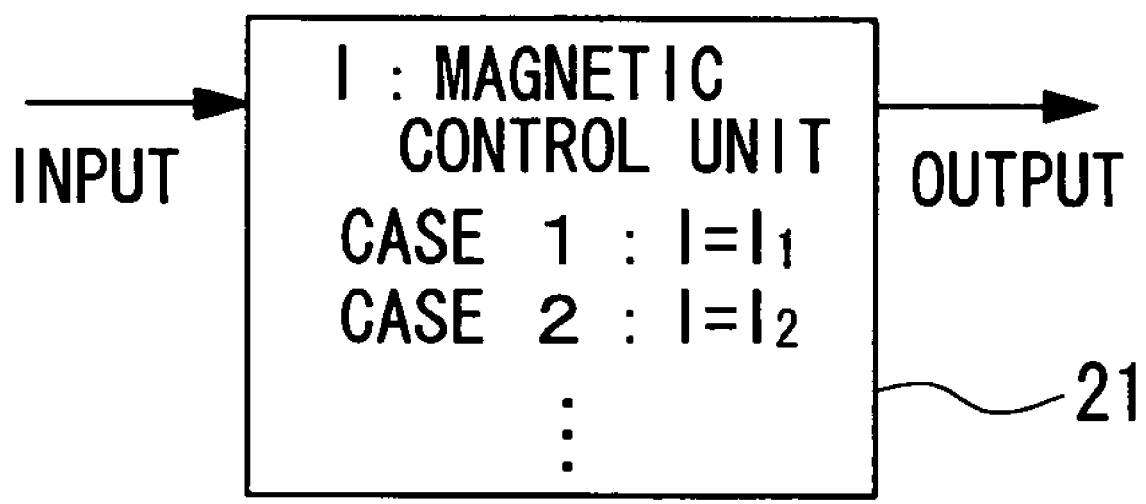
FIG. 4 is a view of selection of the magnetic field pattern shown in FIG. 3.

FIG. 4 is a view showing selection of the magnetic field pattern shown in FIG. 3.

Referring to FIG. 4, a plurality of magnetic field patterns are stored in the magnetic field control unit 21. Based on the information input to the magnetic field control unit 21, the predetermined magnetic field pattern is selected so as to be output.

Figure 5:
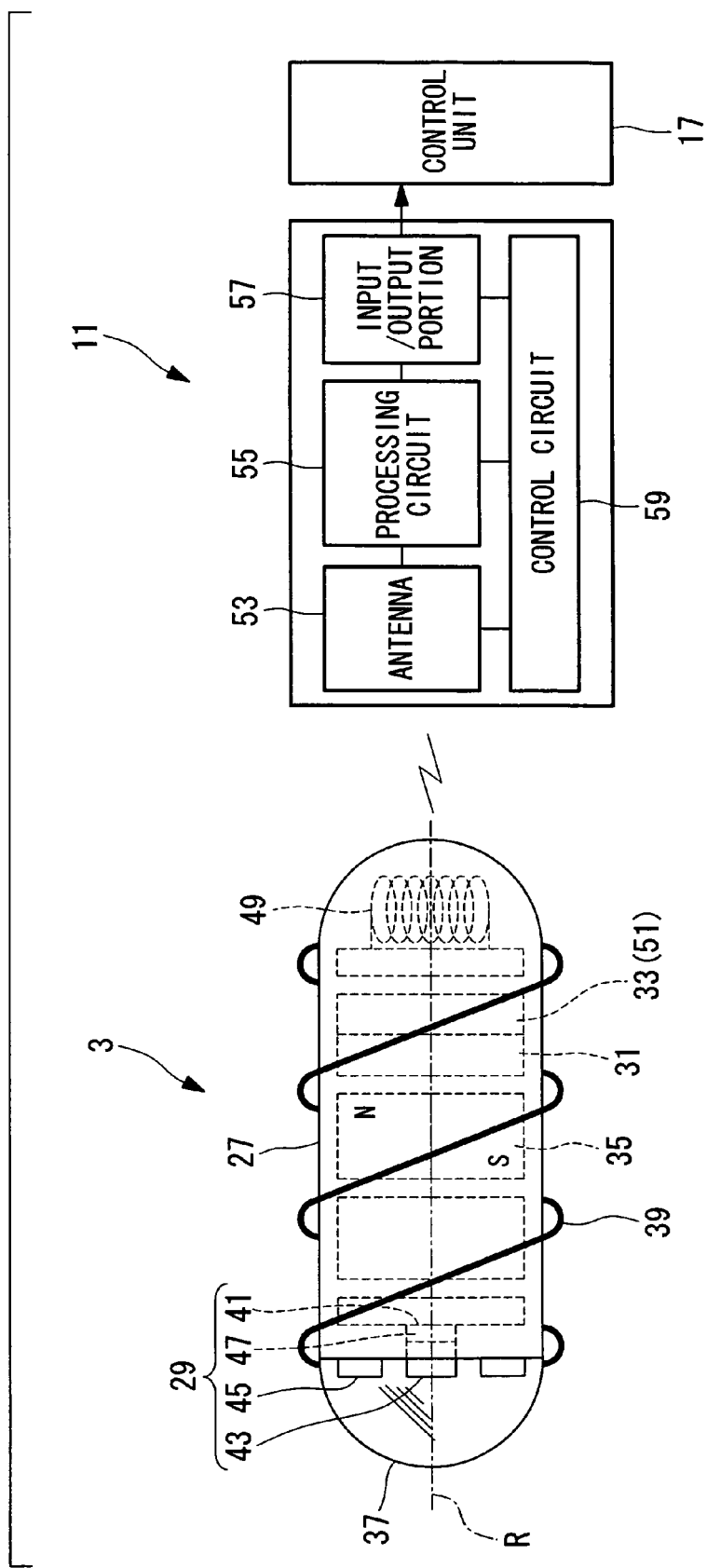
FIG. 5 is a schematic view showing the capsule endoscope and the extracorporeal device shown in FIG. 1.

FIG. 5 is a view schematically showing the capsule endoscope 3 and the extracorporeal device 11 shown in FIG. 1.

Referring to FIG. 5, the capsule endoscope 3 includes an exterior 27 that contains various elements therein, an imaging portion 29 that takes the image of the inner wall of the passage of the subject's body cavity, a battery 31 that drives the imaging portion 29, an induced magnetism generation portion 33 that generates the induced magnetism using the aforementioned triaxial Helmholtz coil 7, and a permanent magnet (magnetic field response portion) 3 as a driving magnet that drives the capsule endoscope 3.

Instead of the permanent magnet 35, an electromagnet may be used as the driving magnet but not limited thereto.

The exterior 27 is formed of a cylindrical capsule body with a rotating axis (insertion direction, center axis) R of the capsule endoscope 3 as the center axis, a hemispherical top cover 37 that covers the leading end of the body, and a hemispherical end that covers the rear end of the body, thus constituting the liquid tight capsule container.

A helical portion (driving force generation portion) 39 formed as a wire material having a circular cross section is provided on the outer peripheral surface while being wound around the rotating axis R.

The helical portion 39 converts the rotation of the capsule endoscope 3 around the rotating axis R into the driving force for forward and reverse movements. In the case where the passage of the cavity is curved, for example, the external force is applied from the wall surface of the cavity of the internal organ. The external force directs the capsule endoscope 3 toward the advancing direction, thus improving the automatic inserting operation.

The imaging portion 29 is formed of a CCD (Charge Coupled Device) 47 that acquires the image of the inner wall surface of the passage of the subject's cavity, a lens that produces the image of the inner wall surface of the passage of the subject's cavity on the CCD 47, an LED (Light Emitting Diode) 45 that illuminates the inner wall surface of the passage of the cavity, a processing circuit 41, and a radio element 49 that sends the image signal to the extracorporeal device 11.

The induced magnetism generation portion 33 includes at least a magnetic induced coil 51 that generates the induced magnetic field through the magnetic field generated by the triaxial Helmholtz coil 7. The magnetic induced coil 51 is disposed such that the center axis substantially accords with the rotating axis R of the capsule endoscope 3. The inner peripheral surface of the magnetic induced coil 51 may be provided with a core member formed of, for example, ferrite. A resonance circuit that contains the magnetic induced coil 51 as the component may also be formed.

Referring to FIG. 5, the extracorporeal device 11 is formed of an antenna 53 that receives the image information transmitted from the capsule endoscope 3, a processing circuit 55 that processes the received image information, an input/output portion 57 that outputs the image information that has been processed to the control unit 17, and a control circuit 59 that control the aforementioned components.

Figure 6A:
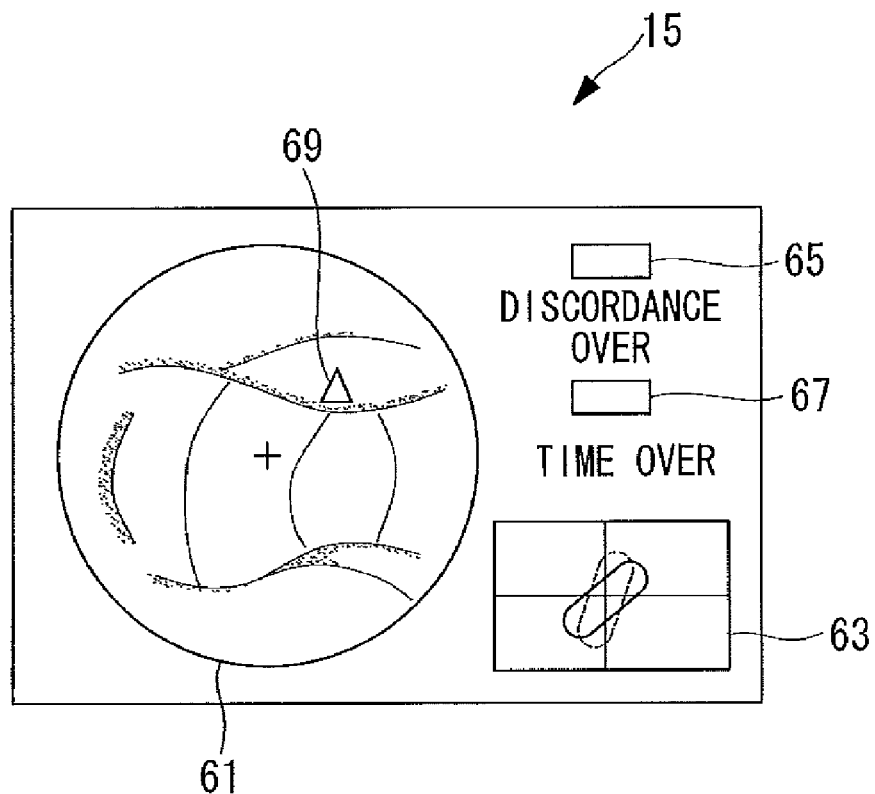
FIG. 6A is an explanatory view of a display on a display unit shown in FIG. 1.
Figure 6B:
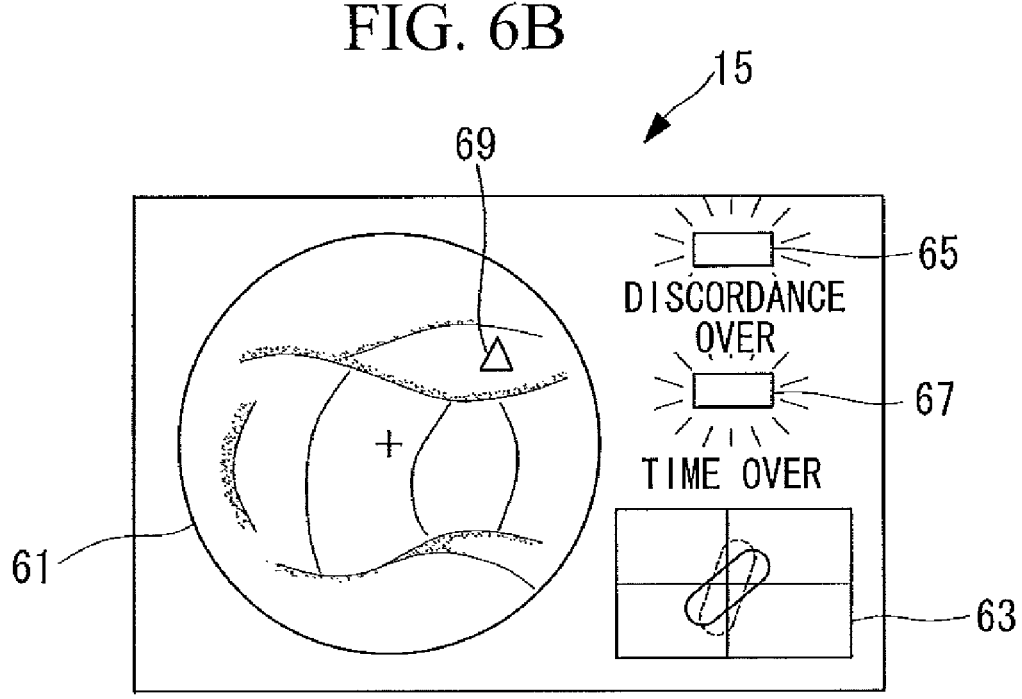
FIG. 6B is an explanatory view of a display to be shown when the discordance exceeds a boundary condition (discordance amount and duration)

FIG. 6A is an explanatory view of the display on the display unit 15. FIG. 6B is an explanatory view on the display when the discordance exceeds the boundary conditions (discordance amount, duration).

Referring to FIG. 6A, the display unit 15 displays an acquired image display 61, an absolute coordinate system display 63, a discordance over display 67, and a time over display 67, respectively.

The acquired image display 61 serves to display the image information that has been taken by the imaging portion 29, on which a cross mark indicating the center of the image and a control direction mark 69 indicating the control direction of the magnetic field are superimposed.

In this way, the control direction is superimposed on the current advancing direction of the capsule endoscope 3. This allows the operator who inputs the control direction to identify the control state intuitively. Accordingly, the operability of the capsule endoscope 3 may be improved.

The absolute coordinate system display 63 has the current direction of the capsule endoscope 3 indicated by the solid line superimposed on the control direction indicated by the broken line.

The discordance over display 65 illuminates when the amount of discordance between the current direction of the capsule endoscope 3 and the control direction exceeds the predetermined boundary condition as shown in FIG. 6B. Likewise, the time over display 67 illuminates when the time elapsed exceeds the predetermined duration in the state where the discordance amount exceeds the predetermined amount.

The display bar indicating the discordance and the boundary condition of the discordance may also be provided. The length of the illuminating portion of the display bar changes in accordance with the discordance.

The amount of the discordance between the direction of the capsule endoscope 3 and the control direction is displayed as described above such that the operator who inputs the control direction may identify the control state easily.

Figure 7A:
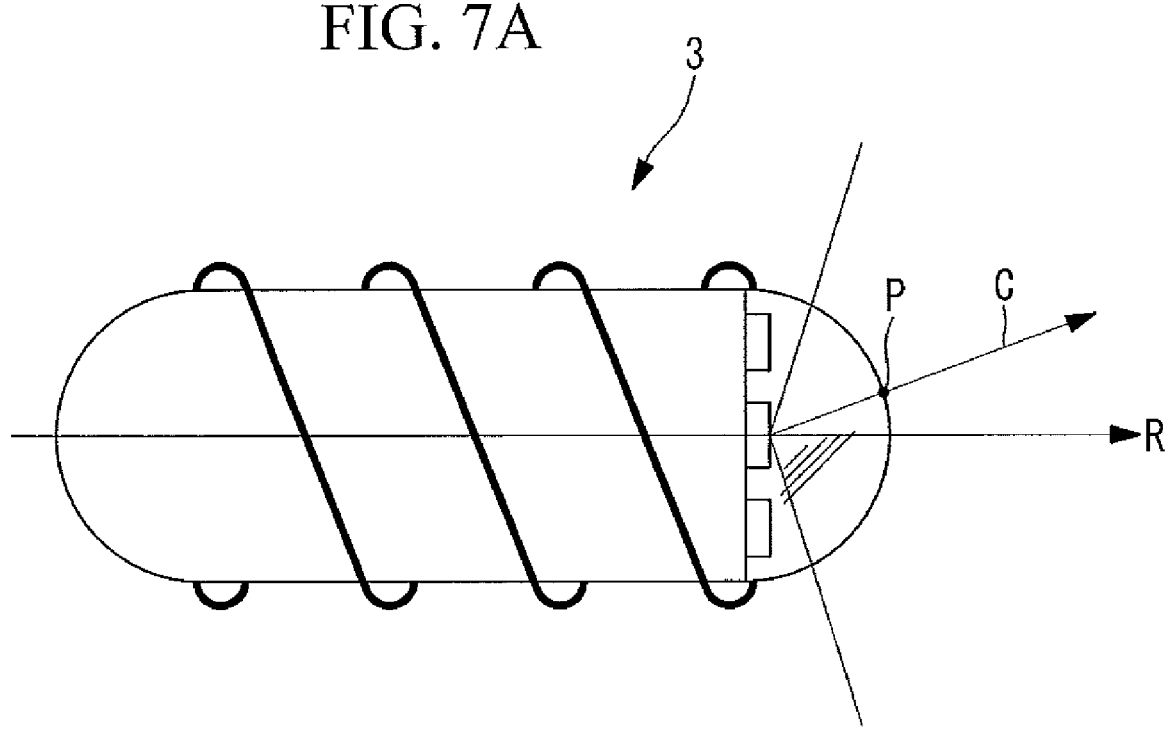
FIG. 7A is a view showing the concept of the control direction displayed on the display unit shown in FIGS. 6A and 6B.
Figure 7B:
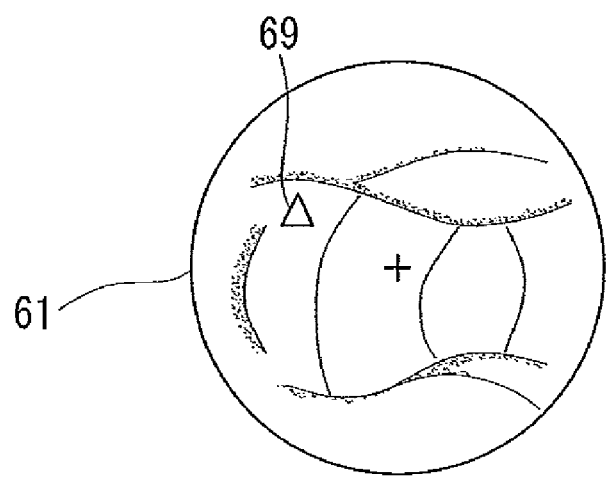
FIG. 7B is a view showing the state where the control direction is displayed on the capture image display.

FIG. 7A is a view showing the concept of the display of the control direction on the display unit 15. FIG. 7B is an explanatory view of the state where the control direction is displayed on the acquired image display 61.

As shown in FIG. 7A, in the state where the control direction C deviates from the direction of the rotating axis R as the advancing direction of the capsule endoscope 3, the control direction mark 69 is displayed at the intersection P of the top cover 37 of the capsule endoscope 3 with the control direction C on the acquired image display 61 (see FIG. 7B).

Figure 8A:
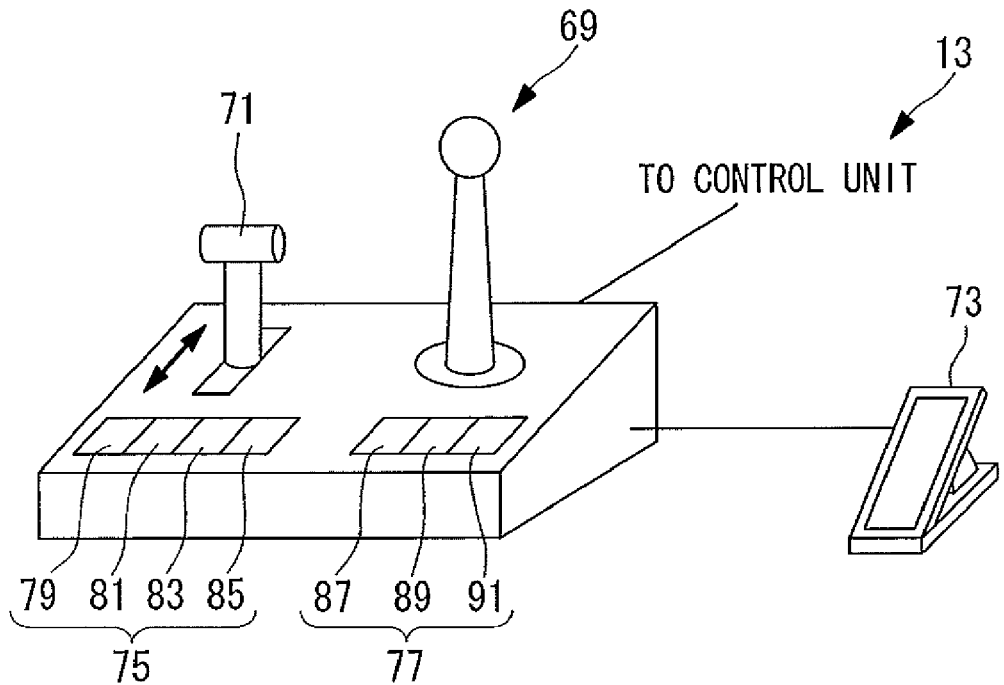
FIG. 8A is a schematic view of the operation unit.

FIG. 8A is a schematic view of the operation unit 13 shown in FIG. 1.

The operation unit 13 includes a direction control lever 69 through which the control information with respect to the direction of the capsule endoscope 3 is input, a forward/reverse lever 71 through which the forward/reverse information is input, an accelerator 73 through which the information of the speed upon forward/reverse movement, a feedback switching portion 75 that switches the process for switching the discordance information, and a magnetic field change pattern switching portion 77 for switching the pattern of the magnetic field generated by the triaxial Helmholtz coil 7.

The feedback switching portion 75 includes an automatic insertion mode switch 79, a discordance information display switch 81, a direction feedback switch 83, and a kinesthetic sense feedback switch 85.

The magnetic field change pattern switching portion 77 includes a normal magnetic field switch 87, a maximum torque switch 89, and a jiggling switch 91.

Figure 8B:
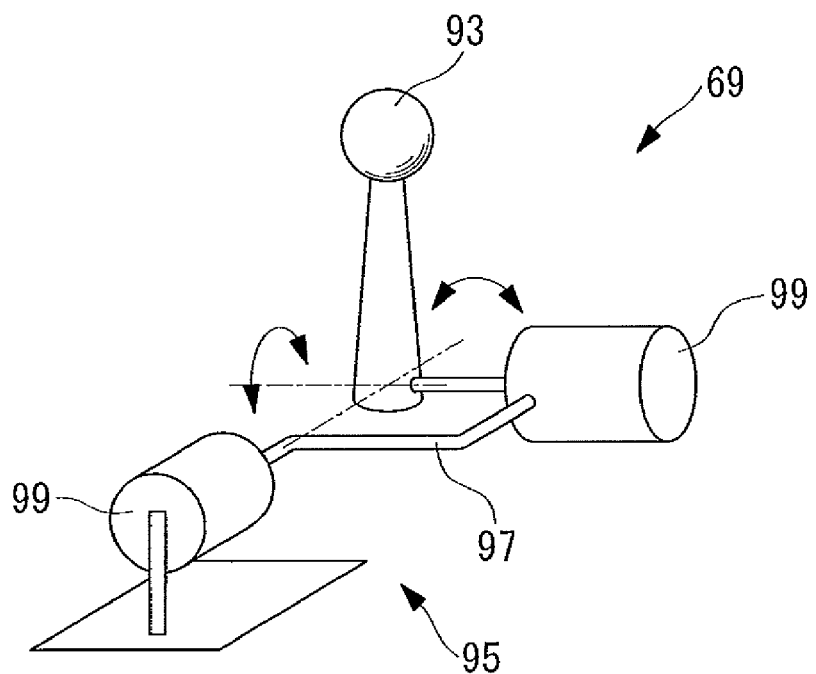
FIG. 8B is a schematic view of the structure of the direction control lever shown in FIG. 8A.

FIG. 8B is a schematic view of the structure of the direction control lever shown in FIG. 8A.

The direction control lever 69 includes a lever body (movable body) 93, and a support portion 95 that rotatably supports the lever body 93. The support portion 95 is provided with a shaft 97 that rotatably supports the lever body 93 around the direction perpendicular to each portion. The support portion 95 includes a feedback portion 99 that is controlled by the control unit 17 based on the discordance information. The feedback portion (the discordance information transmission unit, oscillating body, reaction force generation unit, load generation unit) 99 includes an encoder (not shown) that senses the inclined angle of the lever body 93, and a motor (not shown) that generates the reaction force that inclines the lever body 93 opposite to the inclination thereof.

The motor may be structured to generate the reaction force, or to oscillate the lever body 69. Alternatively, it may be structured to resist against the inclination of the lever body 93.

The use of the above-structured direction control lever 69 allows the feedback portion 99 to transmit the discordance information to the outside through oscillation. Alternatively, the discordance information may be transmitted to the outside as the load against the movement of the lever body 93.

Figure 9A:
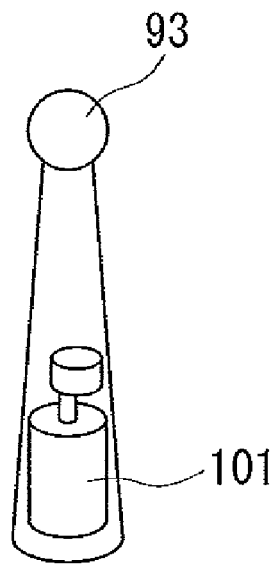
FIG. 9A is an explanatory view of another structure of the direction control lever shown in FIG. 8B.
Figure 9B:
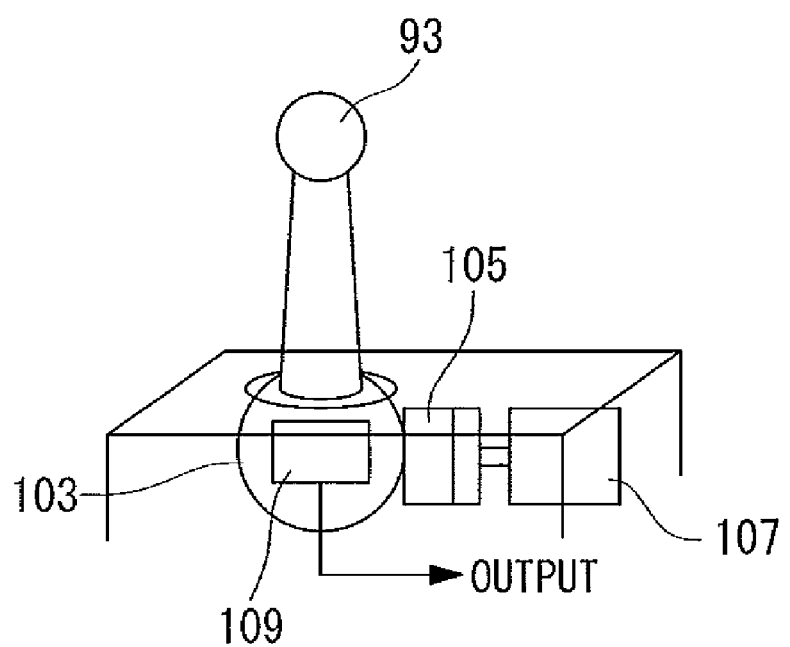
FIG. 9B is an explanatory view of another structure of the direction control lever shown in FIG. 8B.

FIG. 9A is an explanatory view of another exemplary structure of the direction control lever shown in FIG. 8B. FIG. 9B is further exemplary structure of the direction control lever shown in FIG. 8B.

The motor may be disposed as shown in FIG. 8B so as to oscillate the lever body 93. However, an eccentric motor (discordance information transmission portion, oscillating body) 101 may be disposed within the lever body 93 as shown in FIG. 9A, and rotated to oscillate the lever body 93.

The use of the eccentric motor 101 may simplify the structure of the direction control lever 69. The eccentric motor 101 is controlled based on the discordance information so as to change the resonance frequency and range of the resultant oscillation, thus transmitting the discordance information to the operator. For example, the resonance frequency may be increased as the discordance becomes large, and meanwhile, the resonance frequency may be decreased as the discordance becomes small such that the discordance information may be transmitted.

The motor may be disposed as shown in FIG. 8B so as to resist against the inclination of the lever body 93. Alternatively, the lever body 93 may include a spherical body (discordance information transmitting portion, load generation portion) 103, and a friction portion (discordance information transmitting portion, load generation portion) 105 that is urged against the spherical body 103 and a linear actuator 107 that urges the friction portion 105 so as to generate the resisting force using the friction between the friction portion 105 and the spherical boy 103. The spherical body 103 may contain an accelerator sensor 109 such as a gyro therein to detect the inclination of the lever body 93.

The suppressing force applied by the linear actuator 107 is controlled based on the discordance information for the purpose of controlling the friction force between the spherical body 103 and the friction portion 105, thus transmitting the discordance information to the operator. For example, when the discordance becomes large, the load to the movement of the lever body 93 is increased. Meanwhile, when the discordance becomes small, the load is decreased. This makes it possible to transmit the discordance information. The operator is allowed to perform the realistic operation, thus improving the operability of the lever body 93.

The direction control lever 93 may be formed through the easier process compared to the case for generating the reaction force to the movement of the lever body 93.

Figure 10A:
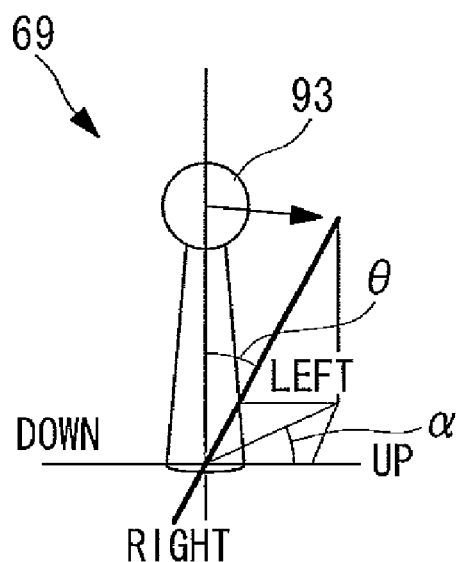
FIG. 10A is an explanatory view showing how the control direction information of the capsule endoscope is input through the direction control lever.
Figure 10B:
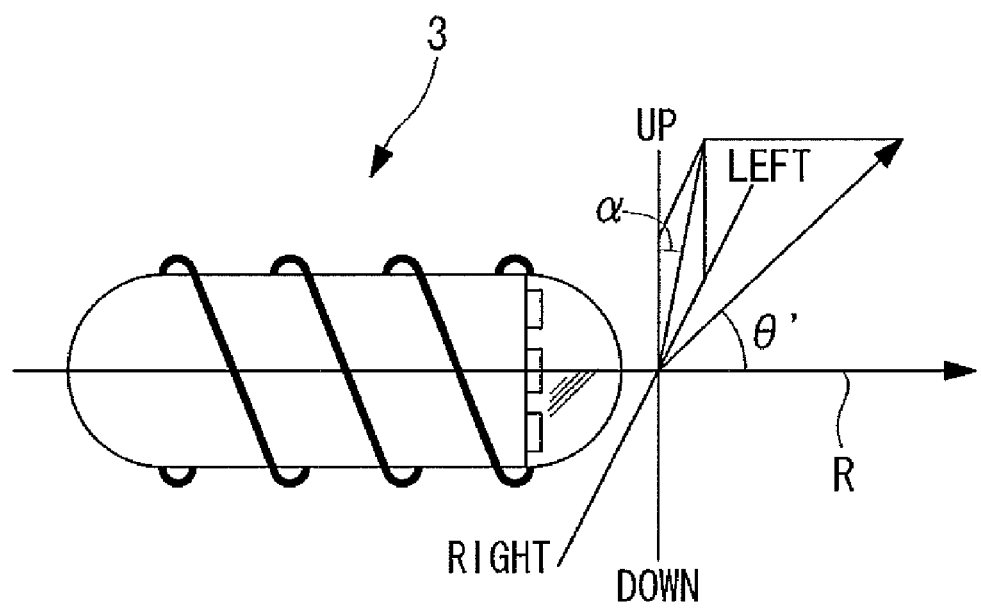
FIG. 10B is an explanatory view showing the control direction of the capsule endoscope based on the control direction information that has been input through the direction control lever.

FIG. 10A is an explanatory view of the control direction information with respect to the capsule endoscope 3 input through the direction control lever 69. FIG. 10B is an explanatory view of the control direction of the capsule endoscope 3 based on the control direction information input through the direction control lever 69.

The direction control lever 69 is operated in upward, downward, left and right directions defined to correspond to those directions (see FIG. 10B) of the rotating axis R of the capsule endoscope 3 as shown in FIG. 10A. When the lever body 93 is inclined at the angle α from the upward to the left direction, the magnetic field is formed to induce the capsule endoscope 3 to be inclined at the angle α from the upward to the left direction.

The angle θ' of the control direction of the capsule endoscope 3 shown in FIG. 10B is controlled based on the inclined angle θ of the lever body 93 shown in FIG. 10A. If the incline angle θ becomes large, the angle θ' becomes large accordingly such that the force for inducing the capsule endoscope 3 to the direction at the angle α is increased.

The respective change patterns of the magnetic field formed by the triaxial Helmholtz coil 7 will be described hereinafter.

Figure 11A:
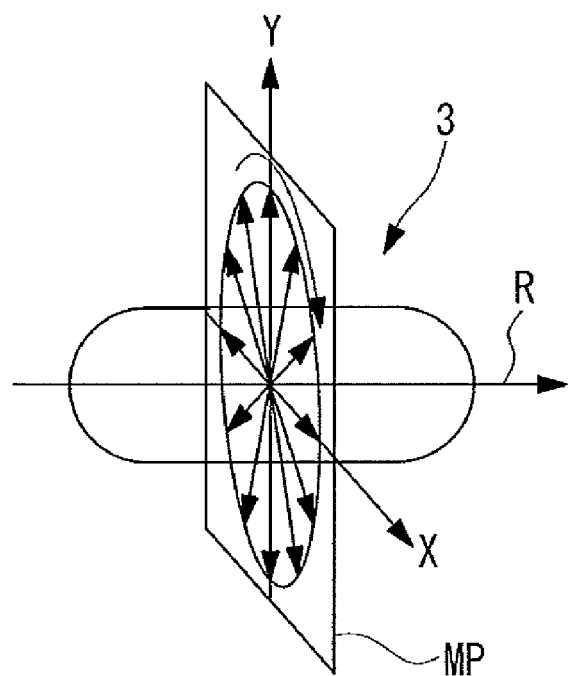
FIG. 11A is an explanatory view of the revolving magnetic field generated around the capsule endoscope in the revolving magnetic field mode.

FIG. 11A is an explanatory view of the revolving magnetic field formed around the capsule endoscope 3 in the revolving magnetic field mode.

The revolving magnetic field mode (normal mode) shown in FIG. 11A indicates the magnetic field change pattern used for controlling the normal capsule endoscope 3, which corresponds to the normal field switch 87 of the operation unit 13.

In the aforementioned mode, the magnetic field revolves in one direction on a revolving magnetic field plane MP. The capsule endoscope 3 is rotated around the rotating axis while holding its position to make the rotating axis R perpendicular to the revolving magnetic field plane MP. When the capsule endoscope 3 moves straight, the control direction of the capsule endoscope 3 substantially accords with the direction of the rotating axis R.

Figure 11B:
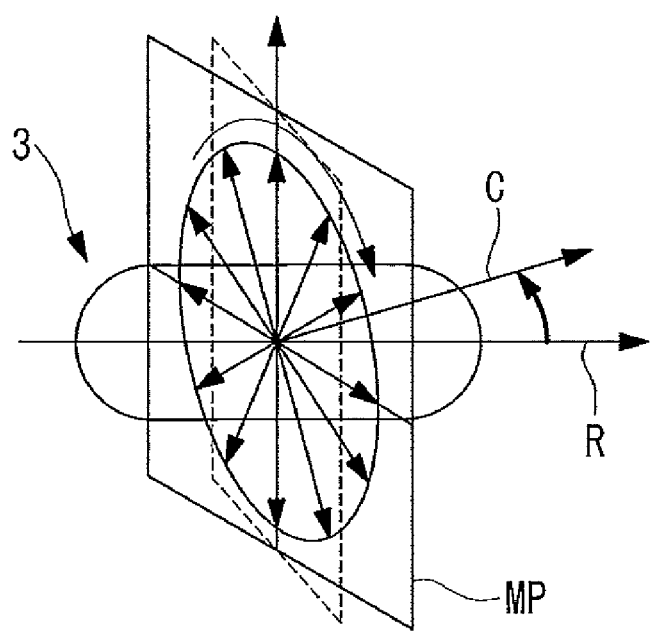
FIG. 11B is an explanatory view of the capsule endoscope that rotates in the revolving magnetic field mode.

FIG. 11B is an explanatory view of the rotation of the capsule endoscope 3 in the revolving magnetic field mode.

The capsule endoscope 3 is rotated by revolving the revolving magnetic field plane MP while turning the magnetic field in one direction. When the revolving magnetic field plane MP is revolved, torque is generated at the permanent magnet 35 installed in the capsule endoscope 3, which continues acting until the rotating axis R of the capsule endoscope 3 becomes perpendicular to the revolving magnetic field plane MP.

Specifically, the torque is not generated so long as the magnetization direction of the permanent magnet 35 is perpendicular to the revolving plane (defined by the rotating axis R and the control direction C) of the capsule endoscope 3. When the magnetization is directed along the revolving plane, the maximum revolving torque is generated. While the magnetization direction is held as described above, the magnitude of the torque changes like the sinusoidal wave.

The capsule endoscope 3 may be rotated around the rotating axis R by allowing the revolving magnetic field to act on the capsule endoscope 3. The thus driven capsule endoscope 3 may be controlled further stably compared to the case that allows the magnetic field formed by combining the revolving magnetic field and oscillating magnetic field (described later), or the revolving magnetic field to act on the capsule endoscope 3.

Figure 12:
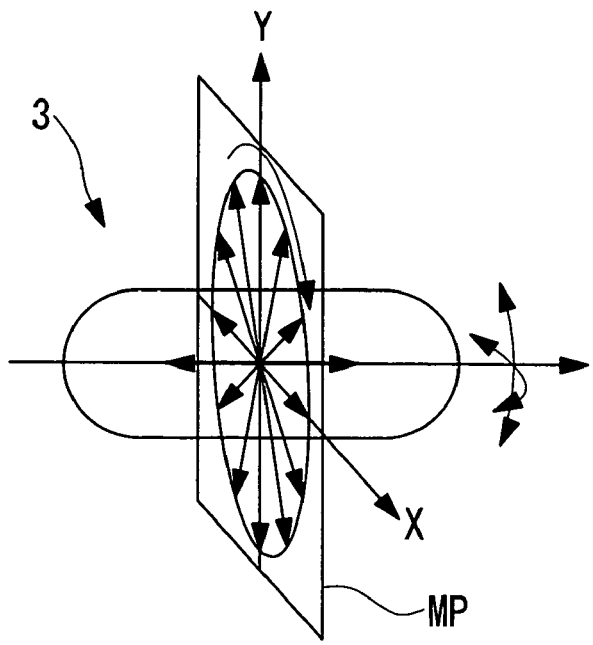
FIG. 12 is an explanatory view of the magnetic field generated in the jiggling mode.

FIG. 12 is an explanatory view of the magnetic field generated around the capsule endoscope 3 in the jiggling mode.

The jiggling mode shown in FIG. 12 has the magnetic field change pattern that swingably rotates the capsule endoscope 3, corresponding to the jiggling switch 91 of the operation unit 13. In this mode, the magnetic field is generated by combining the oscillating magnetic field for oscillating the intensity of the magnetic field and the revolving magnetic field that revolves in one direction on the revolving magnetic field plane MP which is in substantially the same direction as that of the rotating axis R of the capsule endoscope 3. The capsule endoscope 3 rotates around the rotating axis R, and swings in both X and Y directions shown in the drawing. The relationship between the oscillation cycle of the intensity of the magnetic field in the oscillating magnetic field and the revolving cycle of the revolving magnetic field may be controlled to regulate the direction of the swing motion. Further, the rotating axis R is allowed to perform the swing motion (precessional motion) that allows the rotating axis R to rotate around the predetermined axis.

In the case where the capsule endoscope 3 is inserted to move forward through the nearly closed passage of the cavity, for example, the collapsed intestine, the capsule endoscope 3 is swingably rotated to widen the passage of the body cavity so as to further move forward.

Figure 13:
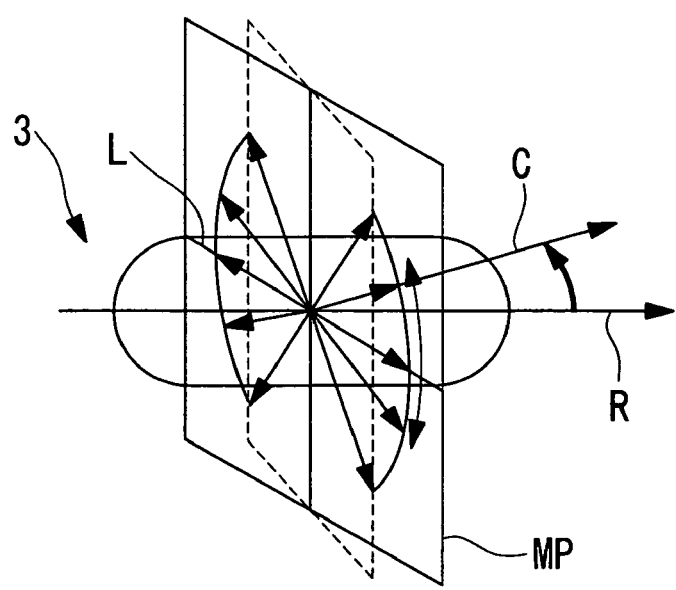
FIG. 13 is an explanatory view of the magnetic field generated in the maximum torque mode.

FIG. 13 is an explanatory view of the magnetic field generated around the capsule endoscope 3 in the maximum torque mode.

The maximum torque mode as shown in FIG. 13 indicates the magnetic field change pattern mainly used for turning the rotating axis R of the capsule endoscope 3, corresponding to the maximum torque switch 89 on the operation portion 13.

The magnetic field in the aforementioned mode functions as the revolving magnetic field that revolves bidirectionally on the revolving magnetic field plane MP in the predetermined angular range with respect to the intersection line L of the revolving magnetic field plane MP with the turning plane (defined by the rotating axis R and the control direction C) of the capsule endoscope 3.

The permanent magnet 35 installed in the capsule endoscope 3 is turned to rotate around the turning plane accompanied with the rotation of the turning magnetic field. This makes it possible to constantly generate the torque that is approximate to the maximum turn torque.

Figure 14:
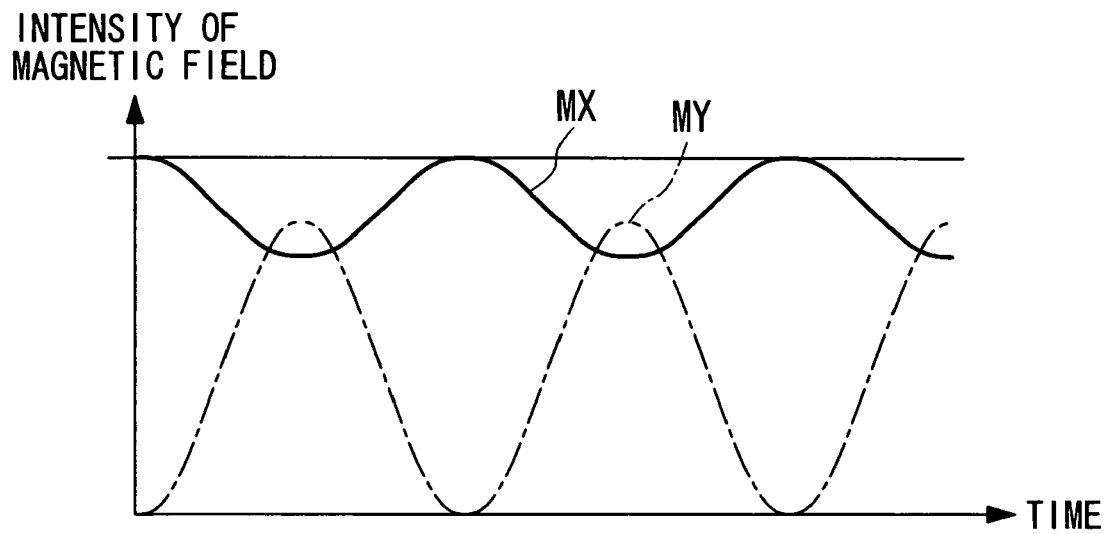
FIG. 14 is an explanatory view of the magnetic field change pattern in the maximum torque mode.

FIG. 14 is an explanatory view of the magnetic field change pattern in the maximum torque mode.

As described above, the revolving magnetic field represents the magnetic field that revolves in the predetermined angular range with the center set to the intersection line L on the revolving magnetic field plane MP. Specifically, it may be represented by an X-axis magnetic field MX, and a Y-axis magnetic field MY as shown in FIG. 14. The axis of abscissas represents time, and axis of ordinate represents the magnitude of the magnetic field of the revolving magnetic field.

The X-axis magnetic field MX may be expressed as the function of, for example, $\cos(\alpha \sin \omega t)$, and Y-axis magnetic field MY may be expressed as the function of, for example, $\sin(\alpha \cos \omega t)$.

As the magnetic field acting on the capsule endoscope 3 functions as the revolving magnetic field where the angle defined by magnetic field direction and the intersection line L becomes equal to or smaller than the predetermined angle, the torque that directs the capsule endoscope 3 toward the control direction C may be generated constantly. Upon change in the direction of the capsule endoscope 3, the torque that directs the capsule endoscope 3 toward the control direction C is constantly generated, thus allowing efficient change in the direction.

The aforementioned mode including the normal mode, jiggling mode, maximum torque mode and the like may be switched through the input to the normal magnetic field switch 87, the maximum torque switch 89, and the jiggling switch 91, respectively.

When the capsule endoscope 3 is under induced control in the normal mode, the mode may be automatically switched based on the information with respect to the discordance between the rotating axis R and the control direction C of the capsule endoscope 3. As the discordance value becomes large, the mode may be switched from the normal mode to the maximum torque mode, and further to the jiggling mode. The mode may further be switched from the normal mode to the jiggling mode, and further to the maximum torque mode.

Likewise the jiggling mode and the maximum torque mode, the other mode besides those aforementioned may be used to improve the turning performance. It is possible to switch the mode in accordance with the time at which the discordance continuously occurs. For example, the mode may be switched when the state where the discordance in excess of the predetermined value continues for a predetermined time or longer.

When the maximum torque mode is switched to the jiggling mode or vice versa, the normal mode is interposed between the maximum torque mode and the jiggling mode.

When the magnetic field change pattern is switched, the magnetic field may be changed intermittently. This may interfere with the stabilized control of the capsule endoscope 3. However, the mode switching is performed via the highly stabilized normal mode (revolving magnetic field) so as to execute the control of the capsule endoscope 3 with high stability.

The respective control modes with respect to the capsule endoscope 3 will be described.

Figure 15:
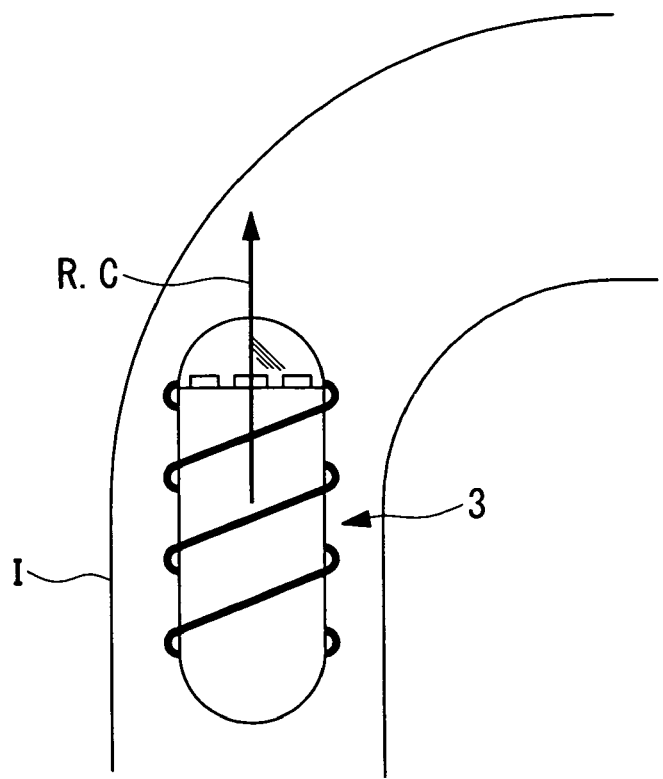
FIG. 15 is a schematic view showing the automatic insertion mode of the capsule endoscope.
Figure 16:
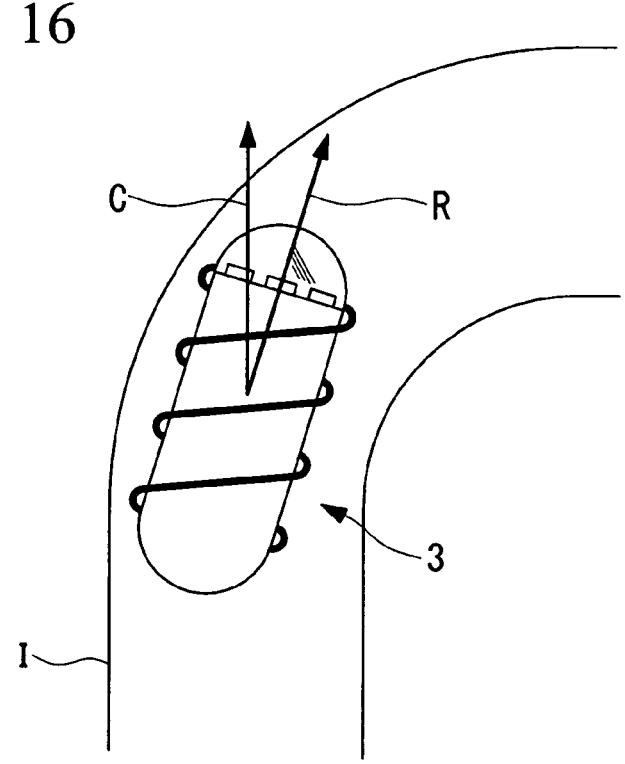
FIG. 16 is a schematic view showing the automatic insertion mode of the capsule endoscope.
Figure 17:
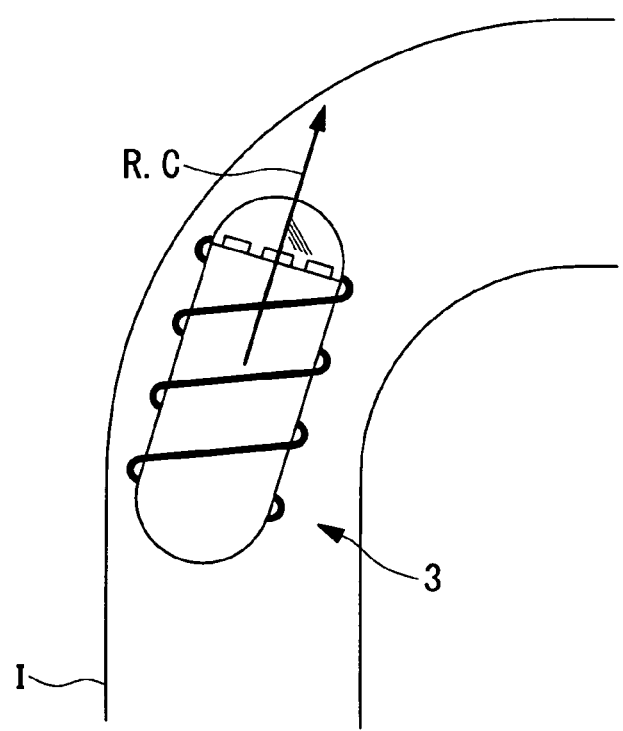
FIG. 17 is a schematic view showing the automatic insertion mode of the capsule endoscope.

Each of FIGS. 15 to 17 schematically shows the automatic insertion mode of the capsule endoscope 3.

Referring to FIGS. 15 to 17, the automatic insertion mode is performed when the discordance between the rotating axis R and the control direction C of the capsule endoscope 3 exceeds the predetermined value so as to accord the control direction C with the rotating axis R of the capsule endoscope 3, which is the control process corresponding to the automatic insertion mode switch 79 on the operation portion 13.

Specifically, in the automatic insertion mode, the capsule endoscope 3 goes forward based on the input through the forward/reverse lever 71 and the accelerator 73 while interrupting the input through the direction control lever 69 of the operation portion 13 (see FIG. 8).

Referring to FIG. 15, in the case where the capsule endoscope 3 is induced within the passage of the body cavity, for example, intestine, the rotating axis R of the capsule endoscope 3 accords with the control direction C at the linear portion of the intestine I.

Referring to FIG. 16, when the capsule endoscope 3 reaches the curved area of the intestine I, the capsule endoscope 3 turns in contact with the intestine wall surface. Then the discordance between the rotating axis R and the control direction C occurs.

When the discordance is increased to exceed the predetermined value, the control direction C is changed to accord with the rotating axis R.

The mode switching operation to the automatic insertion mode may be performed based on the input to the aforementioned automatic insertion mode switch 79 (see FIG. 8). Alternatively, the automatic control mode may be switched from the other control mode when the discordance between the rotating axis R and the control direction C exceeds the predetermined value.

When the discordance increases to reach the predetermined value, the control direction C is changed to accord with the rotating axis R. This makes it possible to allow the capsule endoscope 3 to easily move through the passage of the body cavity along the wall surface thereof.

The control direction C may be adjusted to accord with the rotating axis R directly. Alternatively, the control direction C may be made accorded with the rotating axis R after overshooting in consideration with the elasticity of the intestine wall.

The image acquired by the capsule endoscope 3 is processed such that the advancing direction of the capsule endoscope 3 is extracted. The center of the acquired image is determined as the current advancing direction of the capsule endoscope 3. The control direction may be regulated based on the discordance between the target advancing direction and the current advancing direction of the capsule endoscope 3.

The automatic insertion mode may be realized by generating the magnetic field where the direction obtained by adding the discordance to the current advancing direction of the capsule endoscope is determined as the control direction.

The discordance management control mode will be described.

Figure 18A:
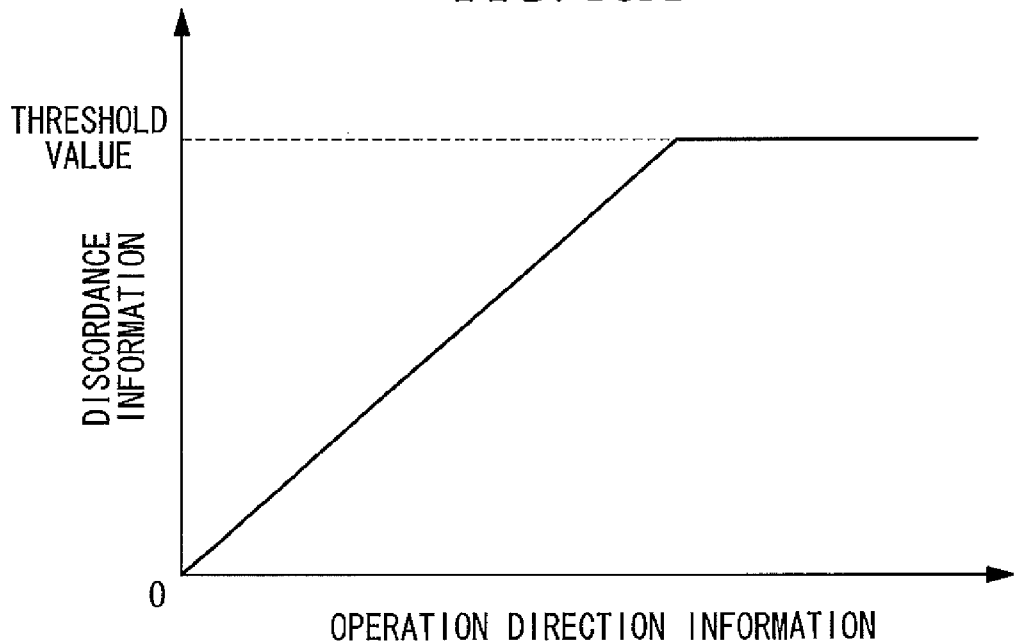
FIG. 18A is an explanatory view of an exemplary discordance management control mode.

FIG. 18A is an explanatory view showing an example of the discordance management control mode.

Referring to FIG. 18A, in the discordance management control mode, the control is executed based on the operation direction information input through the operation control lever 69, and the information of the discordance between the rotating axis R of the capsule endoscope 3 and the control direction.

Specifically, in the case where the rotating axis R of the capsule endoscope 3 fails to follow up with the operation direction information, the size of the discordance information becomes large as the size of the operation direction information becomes large. In this case, however, when the discordance information reaches the predetermined threshold value, the control direction information is fixed to the constant value while interrupting the input of the operation direction information so as to prevent the discordance from exceeding the predetermined threshold value.

The above control prevents the discordance between the rotating axis R and the control direction from being excessively large. If the discordance becomes excessively large, the operation controllability is considerably deteriorated, resulting in, for example, difficulty in the rotation of the capsule endoscope 3 around the rotating axis R. Deterioration in the operation controllability of the capsule endoscope 3 may be prevented by keeping the discordance from being excessively large.

Figure 18B:
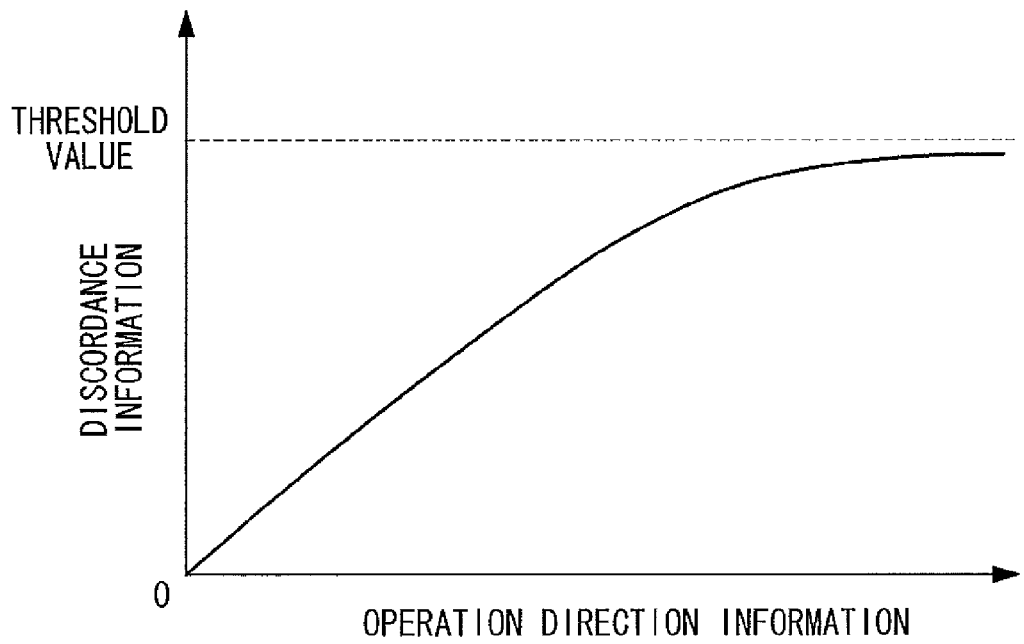
FIG. 18B is an explanatory view of another exemplary discordance management control mode.

FIG. 18B is an explanatory view of another example of the discordance management control mode.

Referring to FIG. 18A, the discordance management control may be executed when the discordance information exceeds the predetermined threshold value. Until then, the control is not executed. Referring to FIG. 18B, the discordance management control may be executed progressively such that the discordance information gradually approaches the predetermined threshold value.

Under the aforementioned control, the operation direction information is gradually interrupted rather than suddenly such that the operator is notified that the discordance information has reached the predetermined threshold value.

Figure 19A:
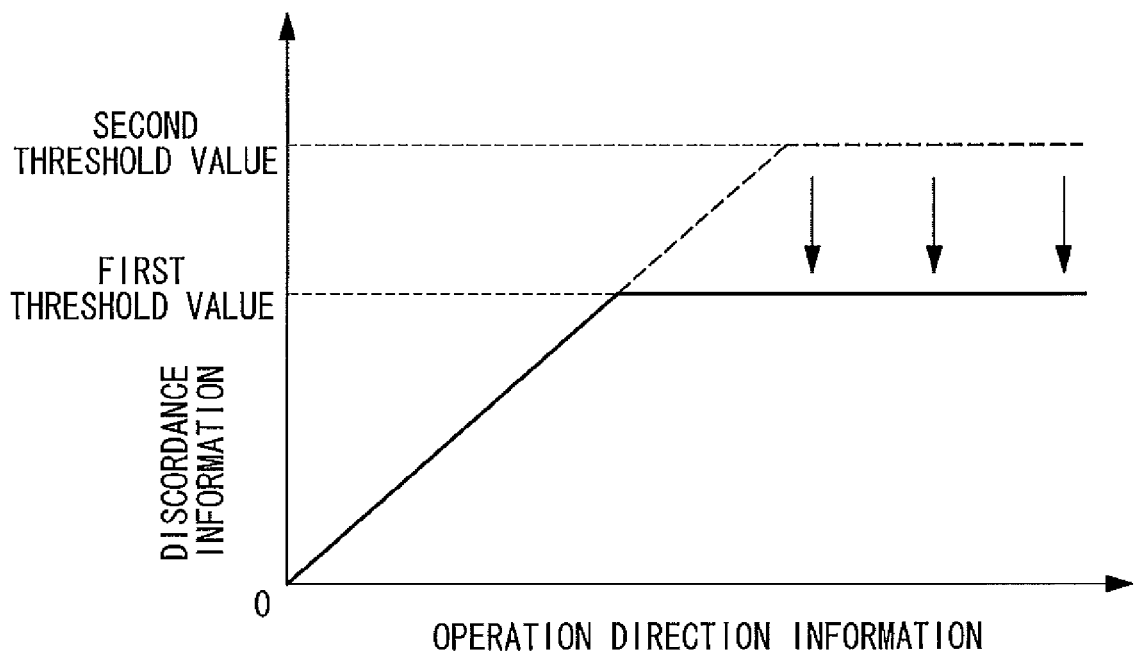
FIG. 19A is an explanatory view of further exemplary discordance management control mode, wherein the axis of abscissas represents the operation direction information input through the direction control lever.
Figure 19B:
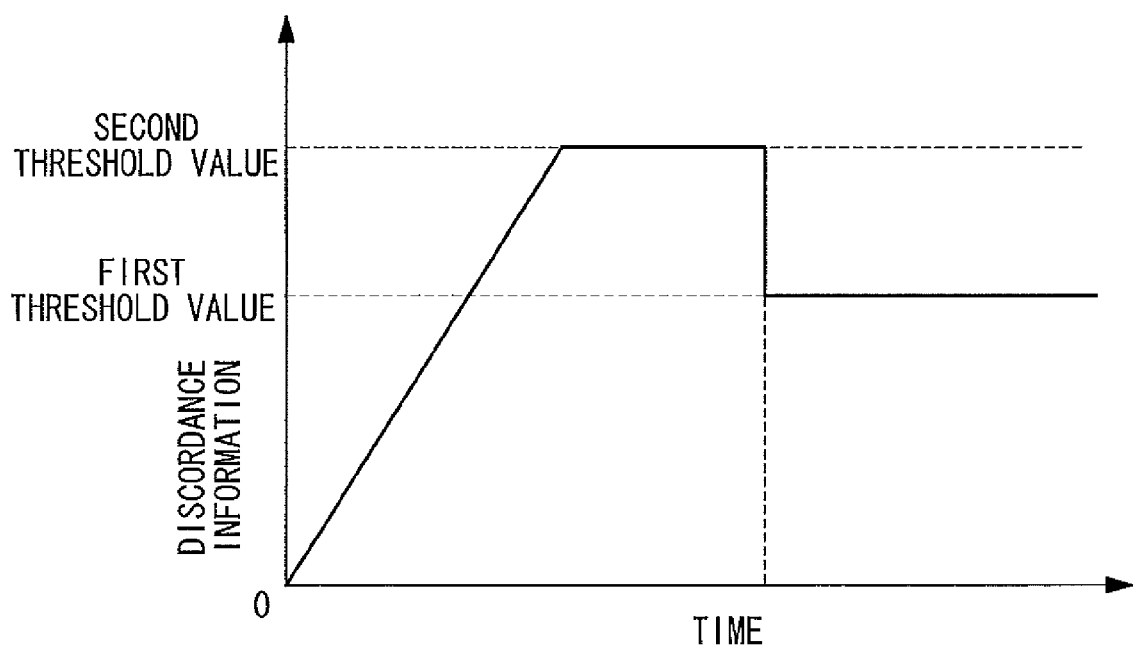
FIG. 19B is an explanatory view of another exemplary discordance management control mode, wherein the axis of abscissas represents time.

Each of FIGS. 19A and 19B is an explanatory view of a further example of the discordance management control mode. FIG. 19A has an axis of abscissas representing the operation direction information input through the direction control lever 69. FIG. 19B has an axis of abscissas representing time.

Referring to FIGS. 19A and 19B, in the exemplary discordance management control mode, when the value of the discordance information reaches the second threshold value, the discordance management control is executed such that the value does not exceed the second threshold value. If the state under the discordance management control continues for a predetermined period of time, the discordance management control is further executed such that the value does not exceed the first threshold value. The first threshold value is smaller than the second threshold value as shown in the drawing.

The discordance management control may be executed by controlling the control direction while regulating the operation direction information as described above. Alternatively, the control may be executed for changing the change pattern of the magnetic field generated by the triaxial Helmholtz coil 7 or the intensity of the generated magnetic field.

The magnetic field change pattern is changed based on the discordance for the purpose of preventing deterioration in operability of the capsule endoscope 3. More specifically, in the case where the magnetic field change pattern is no longer suitable for inducing the capsule endoscope 3 to the control direction, and the discordance becomes too large, the magnetic field change pattern is changed to the one suitable for inducing the capsule endoscope 3, or the intensity of the generated magnetic field is changed so as to prevent the increase in the discordance.

The kinesthetic feedback control process will be described.

Figure 20A:
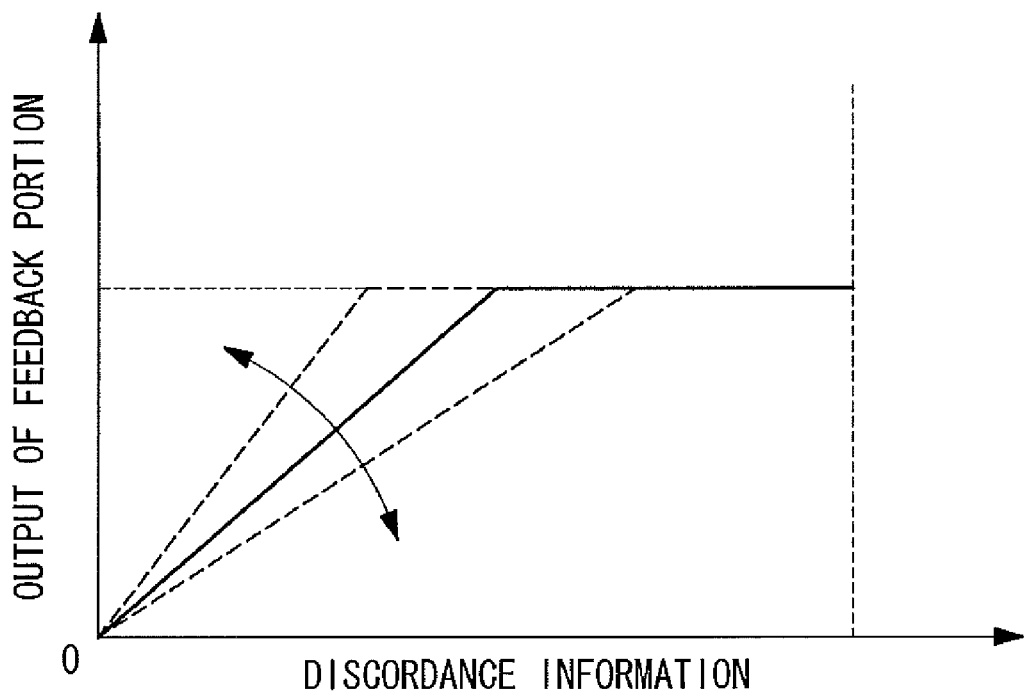
FIG. 20A is a view showing an example of a relationship between the discordance information and the feedback information to the operation unit.

FIG. 20A is a view showing an example of the relationship between the discordance information and the feedback information to the operation unit 13.

Figure 20B:
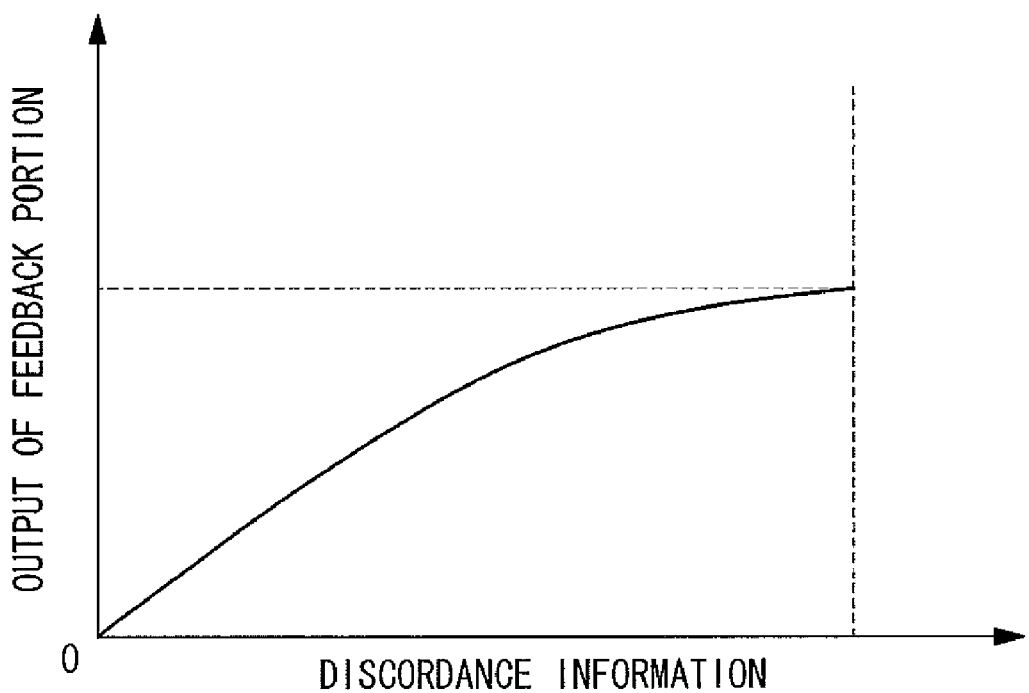
FIG. 20B is a view showing another example of the relationship between the discordance information and the feedback information to the operation unit.

Referring to FIGS. 20A and 20B, the kinesthetic feedback control is executed for adjusting the level of the feedback of the discordance information from the feedback portion 99 of the direction control lever 69 based on the information with respect to the discordance between the rotating axis R of the capsule endoscope 3 and the control direction.

More specifically, under the aforementioned control, the reaction force to the lever body 93 is intensified proportional to the increase in the discordance information, the amplitude of the oscillation transmitted to the lever body 93 is increased, the oscillation cycle is reduced, or the resistance against the action of the lever body 93 is increased.

When the output of the feedback portion 99 reaches the upper limit value, the subsequent output from the feedback portion 99 is controlled to the constant value irrespective of the increase in the discordance information. Thereafter, when the value of the discordance information reaches the predetermined threshold value, the control direction is independently controlled irrespective of the operation direction input information as described with respect to the automatic insertion mode such that the discordance information is prevented from exceeding the threshold value. Alternatively, the control is executed to accord the control direction with the rotating axis R.

The gradient of the ratio of the increase in the discordance information to the level of the discordance information feedbacked from the feedback portion 99 may be arbitrarily changed as dotted lines of FIG. 20A show. The sensitivity of the discordance information feedbacked from the lever body 93 may be changed by adjusting the gradient. This makes it possible to improve the sensitivity by, for example, making the gradient steep.

FIG. 20B is a view of another example of the relationship between the discordance information and the feedback information to the operation portion 13.

As shown in FIG. 20A, the control is kept stopped until the output of the feedback portion 99 reaches the upper limit value. Alternatively, as shown in FIG. 20B, the control may be executed progressively such that the output of the feedback portion 99 gradually approaches the upper limit value.

The aforementioned control allows the relatively small discordance information to be feedbacked with the relatively large output from the feedback portion 99. This makes it possible to prevent the capsule endoscope 3 from being uncontrollable due to the increase in the discordance. When the capsule endoscope 3 is brought into the uncontrollable state in the relatively wide passage of the body cavity like stomach, it is likely to roll down therein. It is preferable to execute the aforementioned control in such a case.

Figure 21:
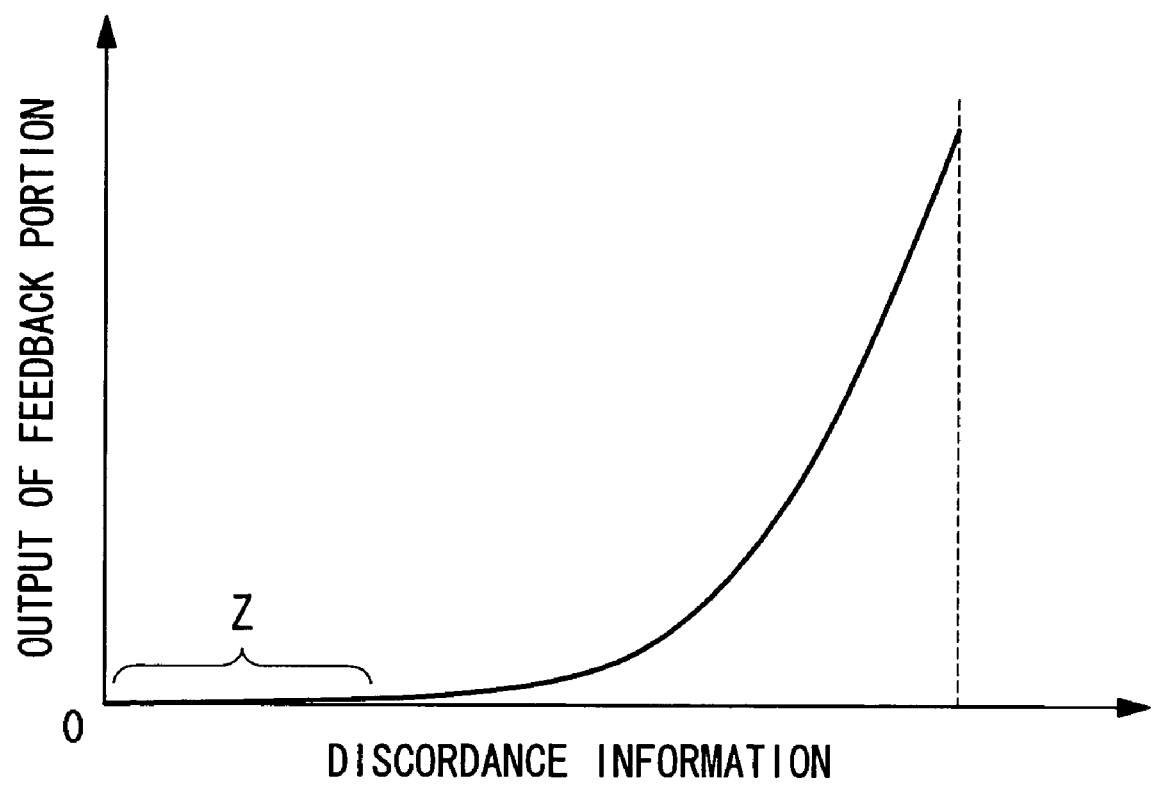
FIG. 21 is a view showing further example of the relationship between the discordance information and the feedback information to the operation unit.

FIG. 21 is a view of another example of the relationship between the discordance information and the feedback information to the operation unit 13.

Referring to FIG. 21, the control for functionally increasing the output of the feedback portion 99 accompanied with the increase in the discordance information may be executed by setting a neutral area Z where the discordance information is small and the signal is not output from the feedback portion 99. When the discordance information value reaches the predetermined threshold value, the control direction is independently controlled irrespective of the input operation direction information as described with respect to the automatic insertion mode so as to prevent the discordance information from exceeding the predetermined value. Alternatively the control may be executed to accord the control direction with the rotating axis R.

While the discordance information is small, the output of the feedback portion 99 is relatively small. Accordingly, a relatively large torque may be easily applied to the capsule endoscope 3. That is, as the discordance information feedbacked to the operator is at the low level, the operator is allowed to perform the input operation without considering the discordance information.

For example, the capsule endoscope 3 may be induced through the narrow passage of the body cavity like the intestine while widening the wall surface of the nearly closed passage. The large torque is required to be applied to the capsule endoscope 3 to widen the nearly closed passage. For this, it is preferable to execute the aforementioned control.

The method for calculating the discordance of the capsule endoscope 3 upon generation of the revolving magnetic field will be described.

Figure 22A:
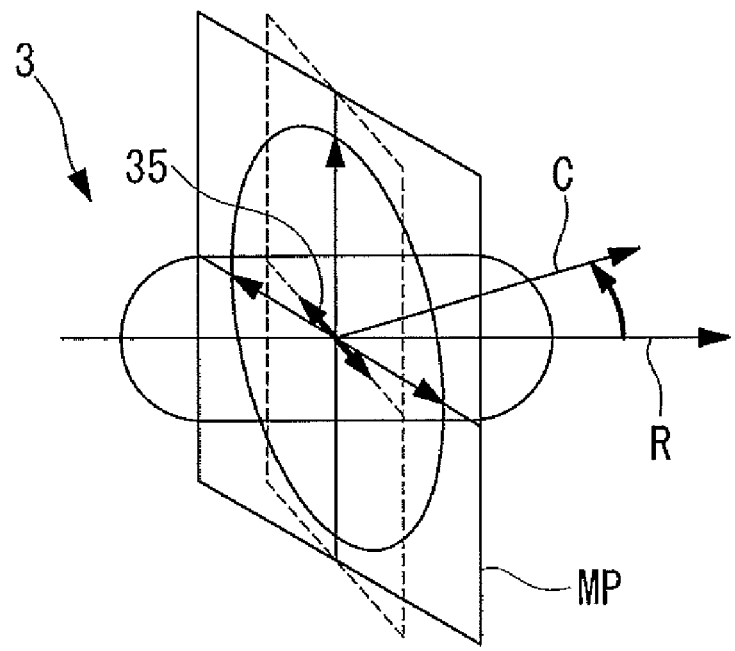
FIG. 22A is an explanatory view showing fluctuation of the torque acting on the capsule endoscope, indicating a positional relationship that maximizes the torque.
Figure 22B:
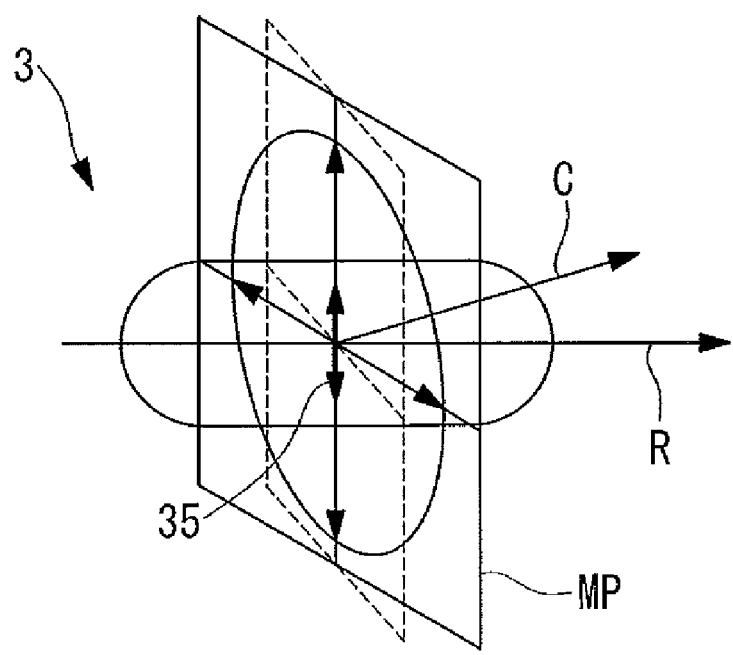
FIG. 22B is an explanatory view showing fluctuation of the torque acting on the capsule endoscope, indicating the positional relationship that minimizes the torque.
Figure 23:
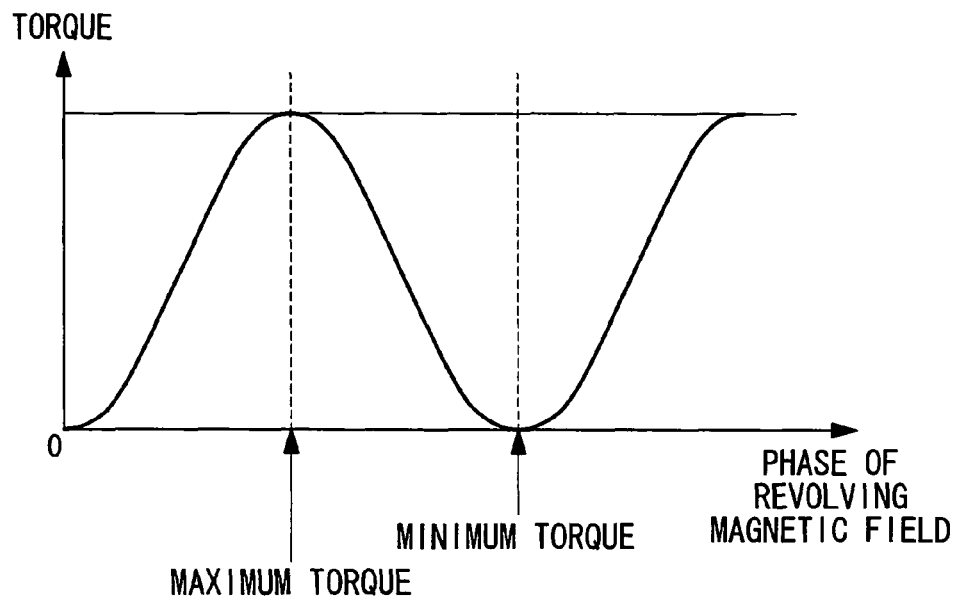
FIG. 23 is an explanatory view of the fluctuation of the torque in the revolving magnetic field.

Each of FIGS. 22A and 22B is an explanatory view of fluctuation in the torque acting on the capsule endoscope 3. FIG. 22A is an explanatory view of the positional relationship that maximizes the torque. FIG. 22B is an explanatory view of the positional relationship that minimizes the torque. FIG. 23 is a view of the relationship between the phase of the magnetic field direction and the intensity of the torque.

The permanent magnet 35 installed in the capsule endoscope 3 rotates accompanied with the revolving magnetic field as shown in FIGS. 22A and 22B. The torque acting on the capsule endoscope 3 is maximized when the magnetic field direction accords with the one along the turning plane defined by the rotating axis R and the control direction C as shown in FIG. 22A. Meanwhile, it is minimized when the magnetic field direction is substantially perpendicular to the turning plane.

The intensity of the torque changes like a sinusoidal wave in the range between the aforementioned maximum and minimum values as shown in FIG. 23. The intensity changes based on the change in the rotating phase in the direction of the revolving magnetic field.

The direction of the capsule endoscope 3 oscillates, that is, discordance occurs in accordance with the change in the intensity of the torque.

In the case where the capsule endoscope 3 is turned toward the elastic wall surface while being in contact therewith, it is pressed to the wall surface when the intensity of the torque becomes high. Meanwhile, the capsule endoscope 3 is pushed back by the elastic wall surface when the intensity of the torque becomes low.

The discordance of the capsule endoscope 3 upon generation of the revolving magnetic field may be calculated based on the average value of the discordances obtained while the revolving magnetic field revolves by half. Alternatively, it may be calculated based on the discordance at the maximum torque.

As the user interface is not influenced by the fluctuation of the discordance owing to the oscillation of the torque, the operability may further be stabilized.

In the aforementioned structure, the control unit 17 controls the user interface 19 based on the discordance. This makes it possible to transmit the information with respect to the discordance to the operator via the user interface 19 (operation unit 13, display unit 15), thus improving both the inducing stability and operability.

Specifically, the information with respect to the discordance is transmitted to the operator from the feedback portion 99. The feedback of the information based on the discordance to the operator may be easily performed, resulting in improved operability of the insertion member.

As the information with respect to the discordance may be displayed on the display unit 15, the discordance information may be transmitted to the operator, thus improving the operability of the capsule endoscope 3.

Figure 24:
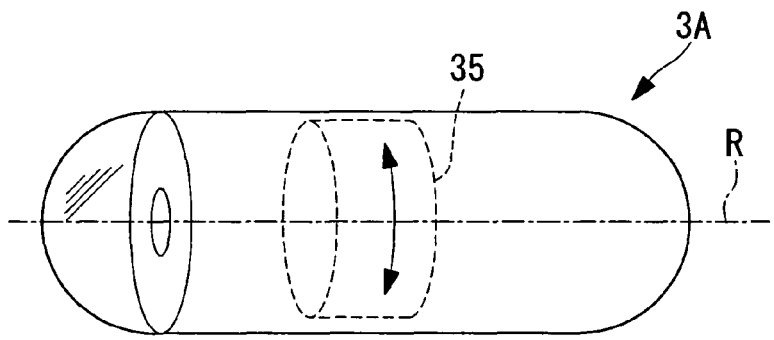
FIG. 24 is a schematic view showing another embodiment of the capsule endoscope shown in FIG. 1.

The permanent magnet 35 may be fixed to the capsule endoscope 3 as described above. Alternatively, it may be rotatably installed on the same axis as the rotating axis R as shown in FIG. 24.

When the revolving magnetic field is caused to act on a capsule endoscope 3A (insertion member, medical device), the permanent magnet 35 rotates accompanied with the revolution of the revolving magnetic field independently from the capsule endoscope 3A. When the direction of the revolving magnetic field plane is changed, the torque is generated at the permanent magnet 35, and transmitted to the capsule endoscope 3A so as to be turned.

The capsule endoscope 3A and the permanent magnet 35 independently rotate around the rotating axis R without influencing other component of the capsule endoscope 3A. This makes it possible to reduce the rotational period of the revolving magnetic field. This makes it possible to reduce the fluctuation cycle of the generated torque in the same way as the capsule endoscope 3.

In the case where the capsule endoscope 3A turns toward the elastic wall surface like the intestinal wall while being in contact therewith, the capsule endoscope 3A oscillates while being pressed against and pushed by the wall surface accompanied with the fluctuation of the torque. In this case, the fluctuation cycle of the torque is reduced to uniformize the oscillation range, thus bringing the oscillation into convergence.

Figure 25:
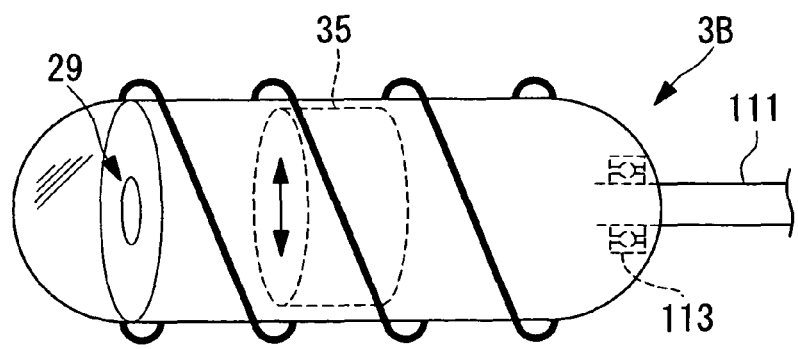
FIG. 25 is a schematic view showing further embodiment of the capsule endoscope shown in FIG. 1.

The capsule endoscope 3 may be formed independently from the external device completely as described above. Alternatively, it may be connected to the external device using a string member 111 at the rear end of a capsule endoscope (insertion member, medical device) 3B as shown in FIG. 25. In this case, a bearing 113 is provided between the string member 111 and the capsule endoscope 3B so as not to transfer the rotation of the capsule endoscope 3B to the string member 111.

The aforementioned structure allows the constant power supply to the capsule endoscope 3B via the string member 111, and the transmission of image data taken by the imaging portion 29 to the outside via the string member 111. Accordingly, the power supply does not have to be installed inside, thus making the capsule endoscope 3B compact. As the image data do not have to be transmitted using radio wave, noise is not contained in the transmission data.

Figure 26A:
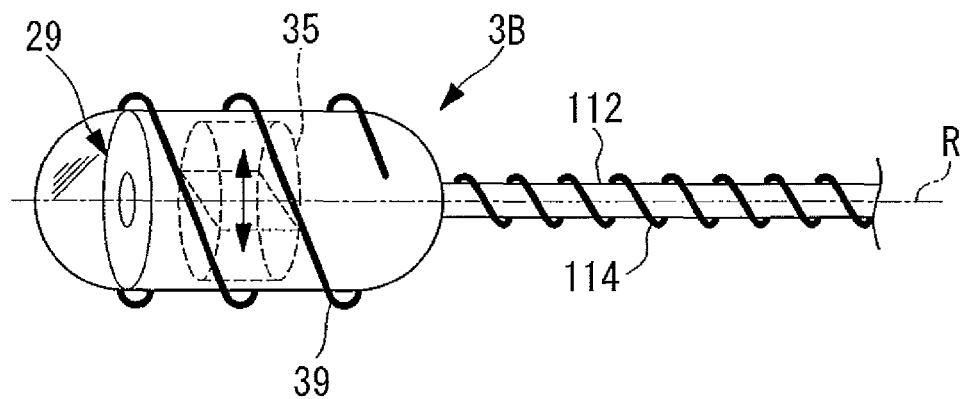
FIGS. 26A, 26B, and 26C are views each showing another embodiment of the capsule endoscope shown in FIG. 1.
Figure 26B:
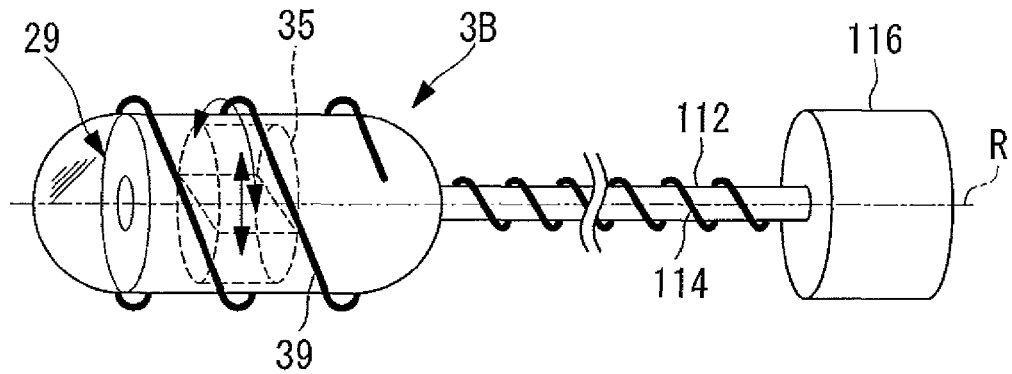

Referring to FIG. 26A, a probe may be formed by providing a string member 112 at the rear end of the capsule endoscope (insertion member) 3B through which the rotating force is transmitted to the capsule endoscope 3B, and a helical member 114 wound around the string member 112. The aforementioned structure generates the driving force at the helical member 114.

Another type of probe may further be formed by providing a motor 116 at the end of the string member 112, and by arranging the permanent magnet 35 and the capsule endoscope 35 so as to be relatively rotated. In the aforementioned structure, the revolving magnetic field is caused to act to regulate the direction of the capsule endoscope 3B. The motor 116 is operated to rotate the probe to generate the driving force at the helical portions 39 and 114.

Figure 26C:
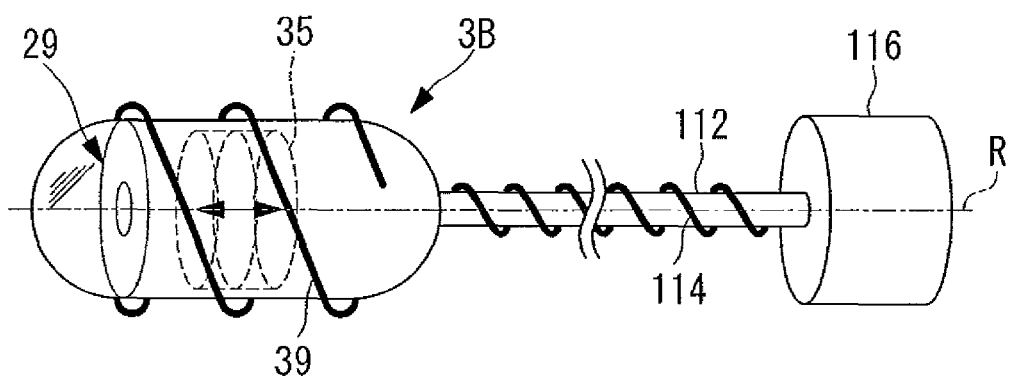

Another type of probe may be formed by providing the permanent magnet 35 with the magnetization direction substantially in parallel to the rotating axis R of the capsule endoscope 3B as shown in FIG. 26C. In the aforementioned structure, parallel magnetic field is caused to act to control the direction of the capsule endoscope 3B. The use of the motor 116 rotates the probe entirely to generate the driving force at the helical portions 39 and 114.

In the aforementioned case, the insertion member to be inserted into the subject's body is formed as the capsule endoscope 3. However, the insertion member is not limited to the capsule endoscope 3. It may be formed as the endoscope (insertion member, medical device) 3C as shown in FIGS. 27A and 27B.

Figure 27A:
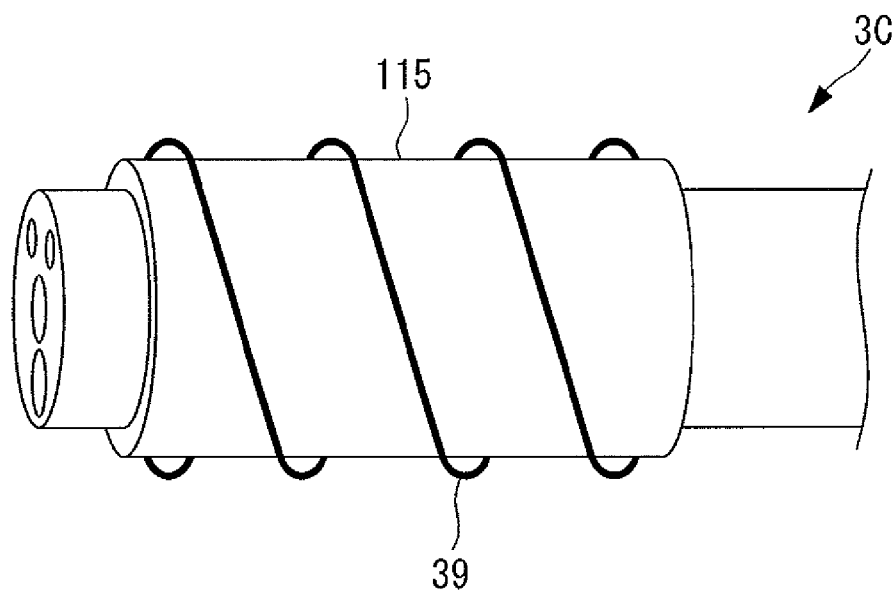
FIGS. 27A and 27B are views each showing an example of the endoscope to which the structure of the capsule endoscope shown in FIG. 1 is applied.
Figure 27B:
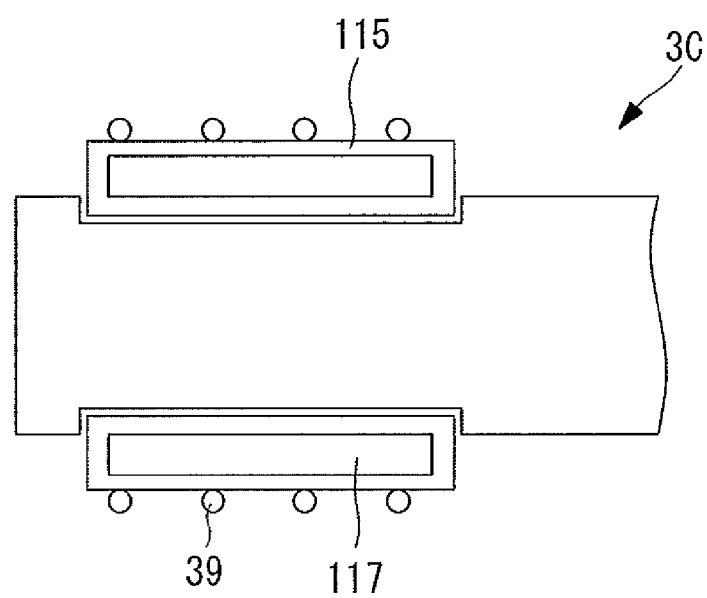

Referring to FIGS. 27A and 27B, the endoscope 3C is rotatably provided with a rotary member 115 which includes a helical member 39 and a magnet 117.

In the aforementioned structure, when the revolving magnetic field acts on the endoscope 3C, the magnet 117 drives to rotate the rotary member 115 such that the helical member 39 provided therearound serves to move the endoscope 3C forward and backward. Likewise the capsule endoscope 3, the direction of the revolving magnetic field plane is controlled to regulate the direction of the endoscope 3C.

Figure 28A:
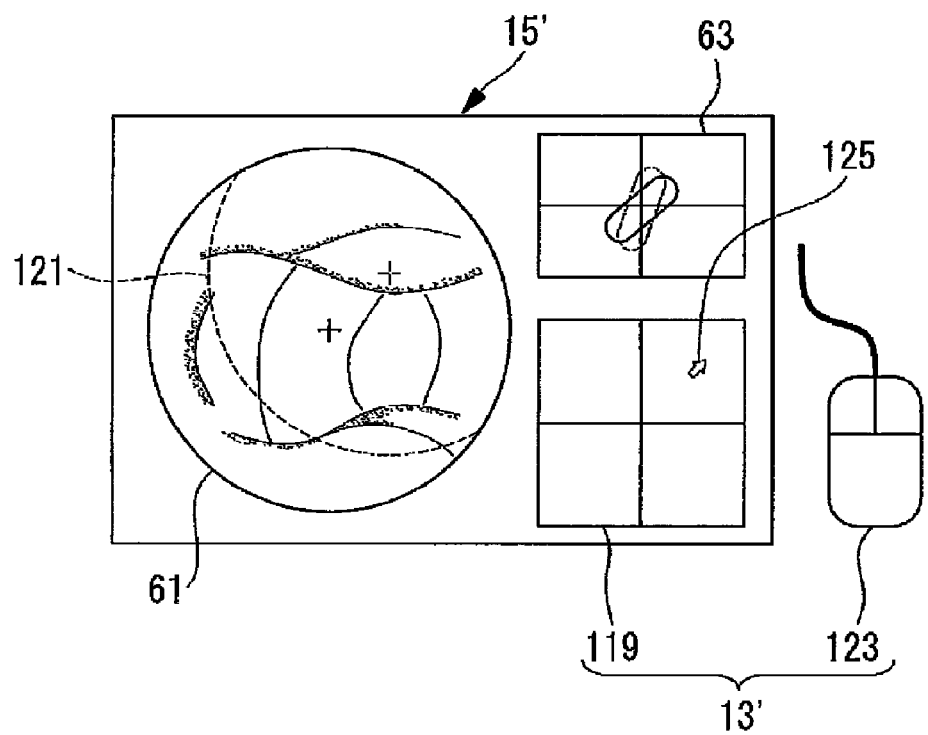
FIGS. 28A, 28B, and 28C are explanatory views each showing another example of the display unit and operation unit shown in FIGS. 6A, 6B, and 8A and 8B, respectively.

The display unit 15 and the operation unit 13 may be formed as shown in FIGS. 6 and 8. A display unit 15' and an operation unit 13' may be formed as shown in FIG. 28A. The display unit 15' includes an acquired image display 61, an entire coordinate system display 63, and an operation display 119 of the operation unit 13' to be described later.

The image information acquired by the imaging portion 29 is displayed on the acquired image display 61, and a control direction mark 121 indicating the direction of the magnetic field (control direction) formed by the triaxial Helmholtz coil 7 is superimposed thereon. The control direction mark 121 includes a cross mark as the center (control direction) and the circle therearound.

The operation unit 13' includes the operation display 119 that displays the operation information, and a mouse 123 through which the operation information is input. The operation display 119 displays a cursor 125 that shows the current control direction.

Figure 28B:
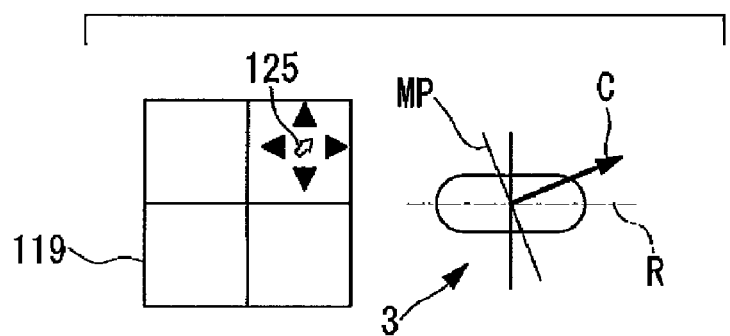
Figure 28C:
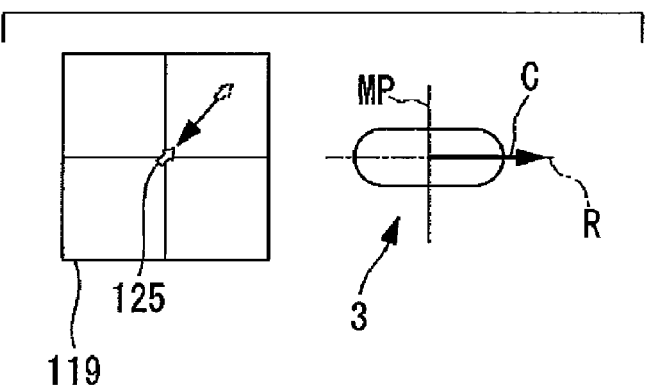

Referring to FIG. 28B, the mouse 123 of the operation unit 13' is operated toward the operation direction of the capsule endoscope 3 while clicking its right button for the purpose of inputting the operation direction information of the capsule endoscope 3. Accordingly, the revolving magnetic field plane MP is controlled to regulate the control direction C.

When the click of the mouse 123 is released, the cursor 125 returns to the center such that the control direction C is controlled to accord with the rotating axis R of the capsule endoscope 3, resulting in straight movement.

The speed of the forward/reverse movement of the capsule endoscope 3 may be input using the wheel of the mouse, for example.

Second Embodiment

A second embodiment of the invention will be described referring to FIGS. 29 to 34.

The structure of a probe control system 201 according to the embodiment of the invention is basically the same as that of the capsule endoscope control system according to the first embodiment except the configuration of the insertion member (probe) to be inserted into the subject's body, and the process for detecting its position. In the present embodiment, the configuration of the probe, and the position detection unit thereof will only be described. The other explanation with respect to the control and the like, thus, will be omitted.

Figure 29:
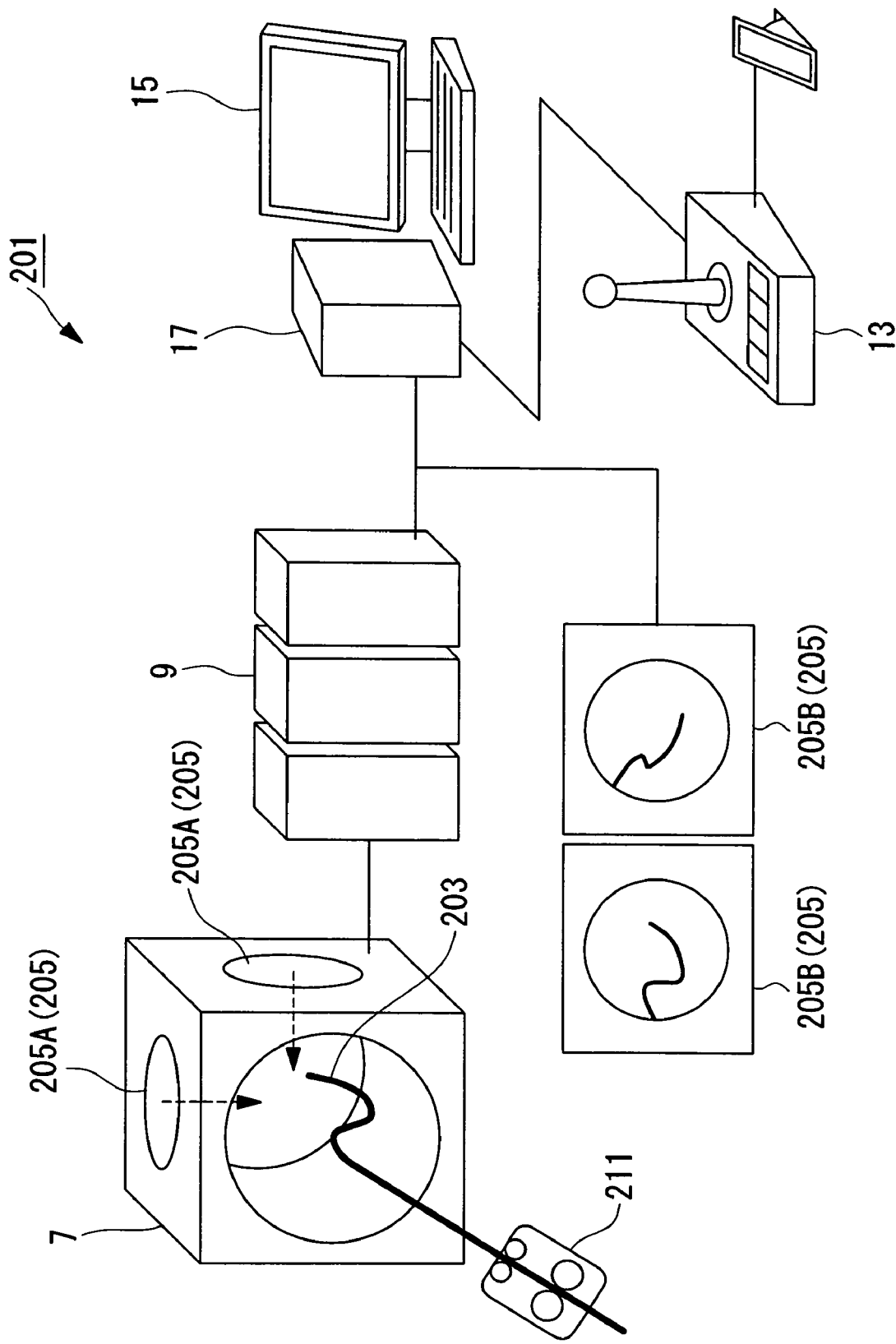
FIG. 29 is a view schematically showing the structure of the probe control system according to the second aspect of the invention.

FIG. 29 is an explanatory view schematically showing a structure of the probe control system according to the embodiment.

The same components as those of the first embodiment are designated as the same reference numerals, and explanations thereof, thus, will be omitted.

The probe control system (medical device control system) 201 includes a probe (insertion member) 203 to be inserted into the subject's body, an X-ray apparatus (direction detector) 205 that detects the information with respect to the position or the direction of the probe 203, a triaxial Helmholtz coil 7 that generates the magnetic field acting on the permanent magnet installed in the probe 203, a power supply 9 that supplies power to the triaxial Helmholtz coil 7, a feeder 211 that feeds the probe 203, an operation unit 13 through which the control information is input to the probe 203, a display unit 15 that displays the image information transmitted from the probe 203, and a control unit 17 that controls the triaxial Helmholtz coil 7, the operation unit 13, and the display unit 15 and the like.

Figure 30:
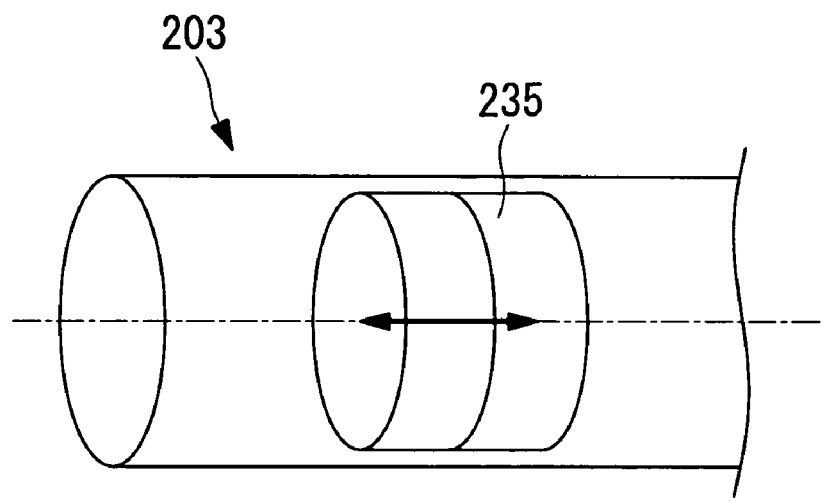
FIG. 30 is an explanatory view of an arrangement of the permanent magnet installed in the probe shown in FIG. 29.

Referring to FIG. 30, the probe 203 contains a permanent magnet 235 therein for controlling the direction of the probe 203. The permanent magnet 235 is provided such that its magnetization direction accords with the longitudinal axis of the probe 203.

Figure 31:
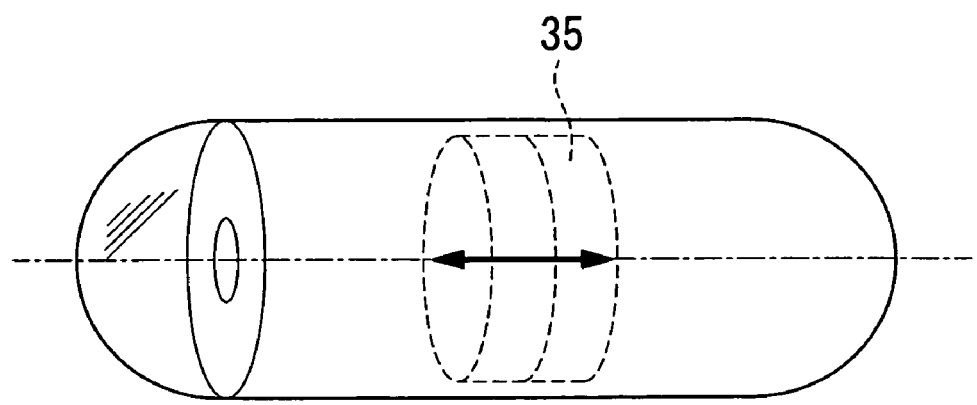
FIG. 31 is an explanatory view showing the structure of the capsule endoscope to which the probe structure shown in FIG. 30 is applied.

The probe 203 may be used as the insertion member as described above, or the capsule endoscope as described in the first embodiment. Referring to FIG. 31, it is preferable to provide the permanent magnet 35 installed in the capsule endoscope such that its magnetization direction accords with the longitudinal axis of the capsule endoscope.

The X-ray apparatus 205 is formed of an image detection unit 205A that detects the position and direction information with respect to the probe 203, and an X-ray image display unit 205B that displays the detected image information.

The control pattern of the probe 203 will be described.

Figure 32:
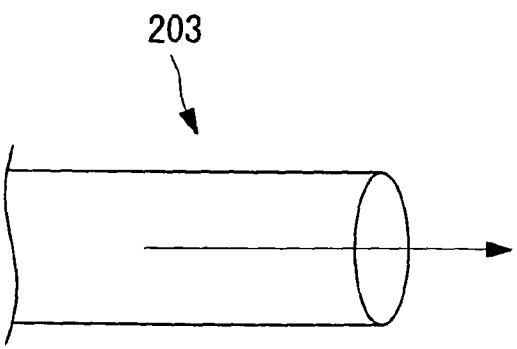
FIG. 32 is an explanatory view showing the state where the parallel magnetic field is generated around the probe.

FIG. 32 is an explanatory view of a magnetic field pattern that controls the direction of the probe 203 to the predetermined direction.

The direction of the probe 203 may be controlled to the predetermined direction by forming a parallel magnetic field around the probe 203 as shown in FIG. 32 such that the direction of the parallel magnetic field accords with the predetermined direction.

The probe 203 is fed by the feeder 211 while controlling the direction of the probe 203 so as to be induced to the predetermined site. The operator performs the inducing operation while confirming the position and direction of the probe 203 displayed on the X-ray image display unit 205B.

Figure 33:
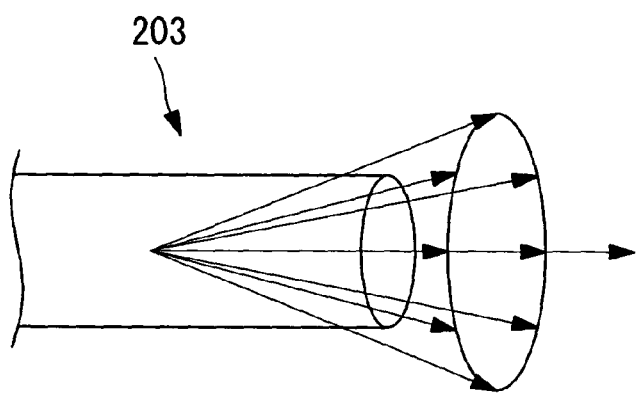
FIG. 33 is an explanatory view showing the state where the conical magnetic field is generated around the probe.

FIG. 33 is an explanatory view of a magnetic field pattern that controls the leading end of the probe 203 to swingably rotate.

Referring to FIG. 33, a conical magnetic field that conically revolves is formed around the probe 203 such that the leading end of the probe 203 is controlled to swingably rotate. The nearly closed passage of the body cavity may be widened by the swingably rotating leading end of the probe, thus easily inducing the probe 203.

As the probe 203 is turned to the predetermined direction while swingably rotating the leading end, the narrow passage may be widened to turn the probe 203.

Figure 34:
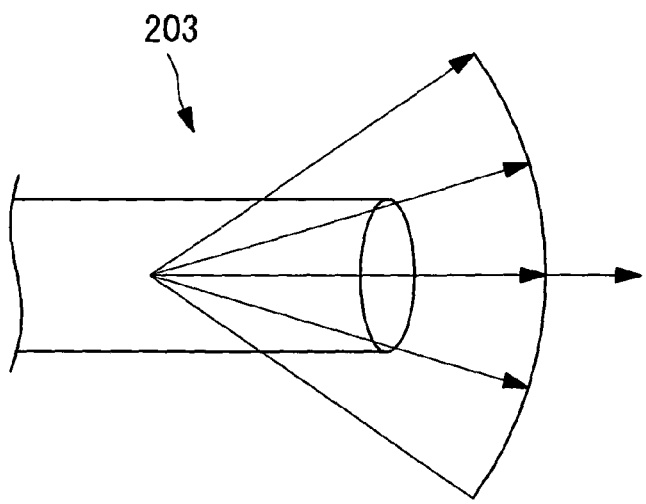
FIG. 34 is an explanatory view showing the state where the swinging magnetic field is combined around the probe.

FIG. 34 is an explanatory view of the magnetic field pattern that controls the leading end of the probe 203 to swingably rotate in one direction.

Referring to FIG. 34, the oscillating magnetic field that swingably oscillates on the predetermined plane is formed to control such that the leading end of the probe 203 is swingably rotated. For example, the leading end of the probe 203 is turned while being swingably oscillated on the same plane as that of turning. This makes it possible to allow the probe 203 to be easily turned even in the nearly closed passage of the cavity. The leading end of the probe 203 may be swingably oscillated on the plane substantially perpendicular to the turning plane such that the probe is allowed to turn even through the nearly closed passage of the cavity.

Upon switching operation from the conical magnetic field to the oscillating magnetic field and vice versa, the parallel magnetic field is formed at the interval between the conical magnetic field and the oscillating magnetic field. The magnetic field is likely to be changed intermittently upon the switching operation, which may deteriorate the control stability of the probe 203. However, the control stability of the probe 203 may be held by inserting the parallel magnetic field with the highest control stability upon the switching operation, resulting in the stabilized control of the probe 203.

The embodiment has been described with respect to the probe as the insertion member to be inserted into the subject's body. However, the endoscope or catheter may be used as the insertion member. The insertion member may be selected from the catheter and endoscope conforming to needs of the diagnosis and treatment, thus allowing suitable medical treatment.

In the aforementioned structure, the probe 203 is directed toward the magnetization. The magnetic field generation means such as the triaxial Helmholtz coil 7 may be simply structured for controlling the direction of the probe 203. Accordingly, the direction of the probe 203 may be easily controlled.

In the medical device control system, the use of the electromagnet or the magnet may simplify the structure of the magnetic field response portion.

In the medical device control system, the insertion member is substantially cylindrical. The magnetic field response portion exhibits the magnetization direction perpendicular to the insertion direction, and is rotatably disposed around the center axis of the substantially cylindrical insertion member.

According to the invention, the direction of the insertion member may be regulated by controlling the revolving plane of the revolving magnetic field while causing the revolving magnetic field to act on the insertion member. That is, the predetermined axial position of the permanent magnet or the electromagnet may be regulated by controlling the revolving plane of the revolving magnetic field. As the relative positional relationship between the predetermined axis and the insertion member is fixed, the direction of the insertion member may be regulated by controlling the predetermined axial position.

In the medical device control system, the magnetic field response portion exhibits the magnetization direction perpendicular to the insertion direction, and is fixed to the insertion member.

According to the invention, the insertion member may be directed toward one direction by causing the magnetic field perpendicular to the insertion direction to act on the magnetic field response portion.

In the medical device control system, the magnetic field response portion exhibits the magnetization direction substantially in parallel to the insertion direction.

According to the invention, the insertion member may be directed toward one direction by causing the magnetic field substantially in parallel to the insertion direction to act on the magnetic field response portion.

In the medical device control system, the insertion member may be formed as one of the catheter and the probe.

According to the invention, the insertion member may be selected from the catheter or probe in accordance with the use in the passage of the subject's cavity for diagnosis or treatment, thus allowing appropriate medical treatment.

In the medical device control system, the insertion member may be formed as one of the endoscope that acquires the image of the subject's body cavity, and the capsule endoscope.

According to the invention, the insertion member may be selected from the endoscope or capsule endoscope in accordance with the use in the passage of the subject's cavity for diagnosis or treatment, thus allowing appropriate medical treatment.

In the medical device control system, the user interface displays the acquired image of the subject's body cavity, as well as the insertion direction of the endoscope or the capsule endoscope superimposed thereon.

According to the invention, the operator is allowed to identify the acquired image displayed on the acquired image display unit as well as the direction information of the insertion member. This makes it possible to acquire a large amount of information at a time, and to improve the operability of the insertion member.

In the medical device control system, the driving force generation portion is formed of a rotary driving portion that rotates the insertion member or the outer surface thereof at one end of the center axis of the substantially cylindrical insertion member, and a helical portion provided on the outer surface of the insertion member around the center axis of the substantially cylindrical insertion member.

According to the invention, the revolving magnetic field is caused to act on the insertion member to rotate the insertion member around the center axis. The helical portion provided on the outer surface rotates accordingly to generate the driving force. This makes it possible to induce the insertion member.

In the medical device control system, the insertion member is formed as the substantially cylindrical capsule endoscope provided with the helical portion on the outer surface of the capsule endoscope around the center axis thereof.

According to the invention, the revolving magnetic field is caused to act on the capsule endoscope to rotate around the center axis. The helical portion provided on the outer surface rotates accordingly to generate the driving force. This makes it possible to induce the insertion member. In the case where the passage of the body cavity is curved, the external force is applied through the wall surface of the passage of the internal organ such that the insertion member is directed toward the penetrating direction, thus improving the automatic insertion operation.

What is claimed is:

1. A medical device control system comprising:
  a medical device including an insertion member inserted into a subject's body and a magnetic field response portion that generates torque in response to a magnetic field applied from outside the subject's body;
  a direction detection unit that detects an insertion direction of the insertion member;
  a user interface through which information with respect to a control of the insertion direction is input and output;
  a magnetic field generation portion that acts on the magnetic field response portion to generate the magnetic field that directs the insertion member to a control direction;
  a user interface control unit that controls the user interface based on a discordance between the control direction and the insertion direction, wherein the user interface is provided with an operation unit through which an operator commands the insertion direction;

the operation unit is provided with a discordance information transmission portion controlled by the user interface control unit for transmitting the discordance to the operator and with a movable body through which the control direction is input; and the discordance information transmission portion comprises a load generating portion that generates a load to a movement of the movable body.

2. The medical device control system according to claim 1, wherein the discordance information transmission portion comprises an oscillating body.

3. The medical device control system according to claim 1, wherein:

the operation unit is provided with a movable body through which the control direction is input; and the discordance information transmission portion comprises a reaction force generation portion that generates a force in a direction opposite a movement of the movable body.

4. The medical device control system according to claim 1, wherein:

the user interface is provided with a display unit that displays the insertion direction and the discordance; and the display unit is controlled by the user interface control unit.

5. The medical device control system according to claim 4, wherein the display unit displays information of the insertion direction and information of the control direction superimposed thereon.

6. The medical device control system according to claim 4, wherein the display unit displays the discordance between the insertion direction and the control direction.

7. The medical device control system according to claim 1, further comprising a magnetic field control unit that controls the magnetic field generation portion, wherein the magnetic field control unit controls the magnetic field generation portion such that a value of the discordance is equal to or smaller than a predetermined value.

8. The medical device control system according to claim 7, wherein the magnetic field control unit includes a predetermined value change portion that changes the predetermined value with a finite value.

9. The medical device control system according to claim 1, wherein the insertion member includes a driving force generation portion that generates a driving force in the insertion direction.

10. A medical device control system comprising:

a medical device including an insertion member inserted into a subject's body, having its direction controlled by magnetism, and a magnetic field response portion disposed within the insertion member for generating torque in response to a magnetic field applied from outside the subject's body;

a direction detection unit that detects an insertion direction of the insertion member;

a user interface through which a control direction for the insertion direction is input by an operator;

a magnetic field generation portion that generates a magnetic field that acts on the magnetic field response portion;

a magnetic field control unit that controls the magnetic field generation portion based on a discordance between the insertion direction and the control direction;

a user interface control unit that controls the user interface based on a discordance between the control direction and the insertion direction;

wherein the user interface is provided with an operation unit through which an operators command the insertion direction;

the operation unit is provided with a discordance information transmission portion controlled by the user interface control unit for transmitting the discordance to the operator and with a movable body through which the control direction is input; and the discordance information transmission portion comprises a load generating portion that generates a load to a movement of the movable body.

11. The medical device control system according to claim 10, wherein the magnetic field control unit includes:

a magnetic field pattern storage portion that stores a plurality of magnetic field generation patterns, and a magnetic field pattern change portion that selects a magnetic field pattern from the plurality of magnetic field generation patterns so as to be generated based on the discordance, and changes the magnetic field pattern generated by the magnetic field generation portion to the selected magnetic field pattern.

12. The medical device control system according to claim 11, wherein:

the magnetic field response portion comprises one of a magnet and an electromagnet that exhibits a magnetization direction substantially perpendicular to the insertion direction; and one of the plurality of magnetic field patterns stored in the magnetic field pattern storage portion comprises a revolving magnetic field that revolves on a plane substantially perpendicular to the control direction.

13. The medical device control system according to claim 12, wherein:

the insertion member is substantially cylindrical; and the insertion member is provided with the magnetic field response portion rotatably around a center axis of the insertion member.

14. The medical device control system according to claim 12, wherein the magnetic field response portion is fixed to the insertion member.

15. The medical device control system according to claim 11, wherein:

the magnetic field response portion comprises one of a magnet and an electromagnet that exhibits a magnetization direction substantially perpendicular to the insertion direction; and one of the plurality of magnetic field patterns stored in the magnetic field pattern storage portion comprises a magnetic field formed by combining a revolving magnetic field that revolves on a plane substantially perpendicular to the control direction and an oscillating magnetic field that oscillates substantially in parallel to the control direction.

16. The medical device control system according to claim 11, wherein:

the magnetic field response portion comprises one of a magnet and an electromagnet that exhibits a magnetization direction substantially perpendicular to the insertion direction;

one of the plurality of magnetic field patterns stored in the magnetic field pattern storage portion comprises a fluctuating magnetic field having its direction fluctuated on a plane substantially perpendicular to the control direction; and an angle formed by an intersection line of a plane substantially perpendicular to the control direction with a plane that contains the insertion direction and the control direction, and the magnetic field direction of the fluctuating magnetic field varies within a predetermined range.

17. The medical device control system according to claim 16, wherein:
an intensity of the fluctuating magnetic field is kept constant, and an angle formed by the direction of the fluctuating magnetic field, and the intersection line varies continuously within a predetermined range.

18. The medical device control system according to claim 11, wherein the magnetic field pattern change portion generates a magnetic field pattern having the magnetic field revolved on a plane substantially perpendicular to the insertion direction subsequent to the magnetic field pattern currently generated by the magnetic field generation portion, and further generates a next magnetic field pattern thereafter.

19. The medical device control system according to claim 11, wherein:
the magnetic field response portion comprises one of a magnet and an electromagnet that exhibits a magnetization direction substantially in parallel to the insertion direction;
one of the plurality of the magnetic field patterns stored in the magnetic pattern storage portion comprises an oscillating magnetic field that oscillates around the control direction; and
an angle formed by the oscillating magnetic field and the control direction is within a predetermined range.

20. The medical device control system according to claim 19, wherein:
the magnetic field response portion comprises one of a magnet and an electromagnet that exhibits a magnetization direction substantially in parallel to the insertion direction; and
one of the plurality of magnetic field patterns stored in the magnetic field pattern storage portion comprises the magnetic field formed by combining the magnetic field substantially in parallel to the insertion direction and a revolving magnetic field that revolves on a plane substantially perpendicular to the insertion direction.

21. The medical device control system according to claim 19, wherein:
the magnetic field response portion comprises one of a magnet and an electromagnet that exhibits a magnetization direction substantially in parallel to the insertion direction; and
one of the plurality of magnetic field patterns stored in the magnetic field pattern storage portion comprises a fluctuating magnetic field having its direction fluctuated on a plane that contains the insertion direction and the control direction.

22. The medical device control system according to claim 19, wherein:
the magnetic field response portion comprises one of a magnet and an electromagnet that exhibits a magnetization direction substantially in parallel to the insertion direction; and
one of the plurality of magnetic field patterns stored in the magnetic field pattern storage portion comprises a fluctuating magnetic field having its direction fluctuated on a plane perpendicular to a plane that contains the insertion direction and the control direction.

23. The medical device control system according to claim 11, wherein the magnetic field pattern change portion generates a magnetic field pattern having the magnetic field substantially in parallel to the insertion direction subsequent to the magnetic field pattern currently generated by the magnetic field generation portion, and further generates a next magnetic field pattern thereafter.

24. The medical device control system according to claim 10, wherein the magnetic field control unit is provided with a magnetic field intensity change portion that changes an intensity of the magnetic field based on the discordance.

25. A medical device control system comprising:
a medical device including an insertion member inserted into a subject's body, and a magnetic field response portion disposed within the insertion member to generate torque in response to a magnetic field applied from outside the subject's body;
a direction detection unit that detects an insertion direction of the insertion member;
a magnetic field generation portion that acts on the magnetic field response portion to generate a magnetic field for directing the insertion member to a control direction;
a magnetic field control unit that controls the magnetic field generation portion such that a discordance between the insertion direction and the control direction is equal to or smaller than a predetermined value;
a user interface through which information with respect to a control of the insertion direction is input and output;
a user interface control unit that controls the user interface based on a discordance between the control direction and the insertion direction;
wherein the user interface is provided with an operation unit through which an operator commands the insertion direction;
the operation unit is provided with a discordance information transmission portion controlled by the user interface control unit for transmitting the discordance to the operator and with a movable body through which the control direction is input; and
the discordance information transmission portion comprises a load generating portion that generates a load to a movement of the movable body.

26. The medical device control system according to claim 25, wherein when the discordance exceeds the predetermined value, the magnetic field control unit controls the magnetic field generation portion such that the control direction substantially accords with the insertion direction.

27. The medical device control system according to claim 25, wherein the magnetic field control unit is provided with a predetermined value change portion that changes the predetermined value within an effective range.

* * * * *